(12) United States Patent
Bevis et al.

(10) Patent No.: US 7,068,363 B2
(45) Date of Patent: Jun. 27, 2006

(54) SYSTEMS FOR INSPECTION OF PATTERNED OR UNPATTERNED WAFERS AND OTHER SPECIMEN

(75) Inventors: Christopher F. Bevis, Los Gatos, CA (US); Mike Kirk, San Jose, CA (US); Mehdi Vaez-Iravani, Los Gatos, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 255 days.

(21) Appl. No.: 10/456,203

(22) Filed: Jun. 6, 2003

(65) Prior Publication Data

US 2004/0246476 A1 Dec. 9, 2004

(51) Int. Cl.
G01N 21/88 (2006.01)

(52) U.S. Cl. .................................................. 356/237.5

(58) Field of Classification Search .. 356/237.1–237.9, 356/239.3–239.8, 445, 600, 337–339, 614
See application file for complete search history.

(56) References Cited

U.S. PATENT DOCUMENTS

| | | |
|---|---|---|
| 4,889,998 A | 12/1989 | Hayano et al. |
| 5,543,919 A | 8/1996 | Mumola |
| 5,555,472 A | 9/1996 | Clapis et al. |
| 5,555,474 A | 9/1996 | Ledger |
| 5,563,709 A | 10/1996 | Poultney |
| 5,680,207 A | 10/1997 | Hagiwara |
| 5,712,701 A | 1/1998 | Clementi et al. |
| 5,864,394 A | 1/1999 | Jordan, III et al. |
| 5,970,168 A | 10/1999 | Montesanto et al. |
| 5,999,266 A | 12/1999 | Takahashi et al. |
| 6,020,957 A | 2/2000 | Rosengaus et al. |
| 6,021,214 A | 2/2000 | Evans et al. |
| 6,034,776 A | 3/2000 | Germer et al. |
| 6,081,325 A | 6/2000 | Leslie et al. |
| 6,091,493 A | 7/2000 | Stover et al. |
| 6,118,525 A | 9/2000 | Fossey et al. |
| 6,122,047 A | 9/2000 | Stover et al. |
| 6,169,601 B1 | 1/2001 | Eremin et al. |
| 6,201,601 B1 | 3/2001 | Vaez-Iravani et al. |

(Continued)

FOREIGN PATENT DOCUMENTS

DE 4134747 4/1993

(Continued)

OTHER PUBLICATIONS

International Search Report, PCT/US2004/017707, mailed Nov. 5, 2004.

Primary Examiner—Tu T. Nguyen
(74) Attorney, Agent, or Firm—Ann Marie Mewherter; Daffer McDaniel, LLP

(57) ABSTRACT

Systems for inspection of patterned and unpatterned wafers are provided. One system includes an illumination system configured to illuminate the specimen. The system also includes a collector configured to collect light scattered from the specimen. In addition, the system includes a segmented detector configured to separately detect different portions of the light such that azimuthal and polar angular information about the different portions of light is preserved. The detector may also be configured to produce signals representative of the different portions of the light. The system may also include a processor configured to detect defects on the specimen from the signals. In another embodiment, the system may include a stage that is configured to rotate and translate the specimen. In one such embodiment, the system may also include an illumination system configured to scan the specimen in a wide scan path during rotation and translation of the specimen.

39 Claims, 8 Drawing Sheets

U.S. PATENT DOCUMENTS

| | | |
|---|---|---|
| 6,208,411 B1 | 3/2001 | Vaez-Iravani |
| 6,215,551 B1 | 4/2001 | Nikoonahad et al. |
| 6,271,916 B1 | 8/2001 | Marxer et al. |
| 6,288,780 B1 | 9/2001 | Fairley et al. |
| 6,362,923 B1 | 3/2002 | Lange et al. |
| 6,496,256 B1 | 12/2002 | Eytan et al. |
| 6,515,742 B1 | 2/2003 | Ruprecht |
| 6,538,730 B1 | 3/2003 | Vaez-Iravani et al. |
| 6,608,676 B1 | 8/2003 | Zhao et al. |
| 2002/0145732 A1 | 10/2002 | Vez-Iravani et al. |

FOREIGN PATENT DOCUMENTS

| | | |
|---|---|---|
| WO | 98/25131 | 6/1998 |
| WO | 99/45340 | 9/1999 |
| WO | 02/082064 | 10/2002 |

SYSTEMS FOR INSPECTION OF PATTERNED OR UNPATTERNED WAFERS AND OTHER SPECIMEN

BACKGROUND OF THE INVENTION

1. Field of the Invention

This invention generally relates to systems and methods for inspection of a specimen such as a patterned wafer. Certain embodiments relate to inspection systems configured to separately detect different portions of light scattered from a specimen such that angular information about the different portions of the light is preserved.

2. Description of the Related Art

Many different types of inspection tools have been developed for the inspection of semiconductor wafers. The inspection tools may be categorized generally according to the types of specimen that they are designed to inspect. For example, one category of inspection tools is generally designed to inspect unpatterned semiconductor wafers. Since these tools are optimized for inspecting unpatterned wafers, these tools are generally not capable of inspecting patterned wafers for a number of reasons. For example, many unpatterned wafer inspection tools are configured such that all of the light collected by a lens or another collector is directed to a single detector that generates a single output signal representative of all of the light collected by the lens. Therefore, light scattered from patterns or other features on the specimen will be combined with other scattered light. As such, the single detector may become saturated and, consequently, will not yield signals that can be analyzed for defect detection. In addition, even if the single detector does not become saturated, the light scattered from patterns or other features on the wafer can not be separated from other scattered light thereby hindering, if not preventing, defect detection based on the other scattered light.

Patterned wafer inspection is of particular interest and importance to the semiconductor industry because processed semiconductor wafers usually have a pattern of features formed thereon. For example, fabricating semiconductor devices such as logic and memory devices includes processing a semiconductor wafer using a number of semiconductor fabrication processes to form various features and multiple levels of the semiconductor devices. One example of a semiconductor fabrication process is lithography, which typically involves transferring a pattern to a resist arranged on a semiconductor wafer. Additional examples of semiconductor fabrication processes include chemical-mechanical polishing, etch, deposition, and ion implantation. Although inspection of unpatterned wafers, or "monitor wafers," which have been run through a process tool, may be used as a gauge for the number and types of defects that may be found on patterned wafers, or "product wafers," defects detected on monitor wafers do not always accurately reflect the defects that are detected on patterned wafers after the same process in the process tool. Inspection of patterned wafers after such processing is, therefore, important to accurately detect defects that may have been formed on the wafer during, or as a result of, processing.

The results of such inspection may be used to monitor and control semiconductor fabrication processes. Therefore, inspecting patterned wafers or product wafers may provide more accurate monitoring and control of processes and process tools than inspection of monitor wafers. Successful fabrication of semiconductor devices is often limited by the presence of defects in the semiconductor devices. If the fabrication processes can be monitored and controlled for defects, the yield of such processes may be maintained or improved. Furthermore, monitoring semiconductor fabrication processes over time has become increasingly important in the industry to improve or maintain yield as the dimensions of semiconductor devices shrink.

Many inspection tools have been developed for patterned wafer inspection. In many cases, the optical design of such tools can be substantially more complex than that of unpatterned wafer inspection tools. For example, one patterned wafer inspection tool utilizes spatial filters to separate light scattered from patterned features from other scattered light such that the other scattered light may be separately detected. Since the light scattered from patterned features depends on various characteristics of the patterned features such as lateral dimension and period, the design of the spatial filter also depends on such characteristics of the patterned features. As a result, the spatial filter must be designed based on known or determined characteristics of the patterned features and must vary as different patterned features are being inspected. Consequently, although such an inspection tool may provide patterned wafer inspection capability, there are some drawbacks due to the complex optical design.

Accordingly, it may be advantageous to develop a patterned wafer inspection system that has a relatively simple optical design. In addition, it may be advantageous to develop a patterned wafer inspection system that also has unpatterned wafer inspection capability thereby increasing the flexibility of the inspection system, which may become increasingly important as the spatial limitations on inspection tools become more stringent based on clean room costs and for integration of inspection modules into process tools.

SUMMARY OF THE INVENTION

An embodiment of the invention relates to an inspection system that includes an illumination system configured to illuminate a specimen. In some embodiments, the specimen may be a patterned wafer. However, as further described herein, the system may be configured to inspect both patterned and unpatterned wafers and other specimen. The inspection system also includes a collector configured to collect light scattered from the specimen. In one embodiment, an axis of the collector may be centered in the plane of incidence at about 60° from normal to about 80° from normal. In one example, the axis of the collector may be centered in the plane of incidence at about 70° from normal. In another embodiment, the collector may provide a Fourier plane suitable for Fourier filtering of the light.

In addition, the inspection system includes a segmented detector. The segmented detector is configured to separately detect different portions of the collected light such that azimuthal and polar angular information about the different portions of the light is preserved. For example, the system may include a plurality of fibers configured to separately convey the different portions of the light to the detector. In one embodiment, the detector may be an array detector. In another embodiment, the detector may be a multi-anode photo-multiplier tube. The segmented detector may also be configured to produce signals representative of the different portions of the light. The inspection system may further include a processor configured to detect defects on the specimen from the signals.

In some embodiments, the system may also include a side collector. The side collector may be configured to collect light scattered at different azimuthal angles than the collector. In one such embodiment, the system may further include a side segmented detector configured to separately detect different portions of the light collected by the side collector. In this manner, azimuthal and polar angular information about the different portions of light collected by the side collector may be preserved. The side detector may also be configured to produce signals representative of the different portions of the light collected by the side collector.

In one embodiment, the system may include a stage. In some embodiments, the stage may be configured to rotate and translate the specimen during inspection. In other embodiments, the stage may be configured to translate the specimen in two lateral directions during inspection. In an additional embodiment, the illumination system may be configured to illuminate a first surface of the specimen. In such an embodiment, the system may include an optical subsystem configured to detect defects on a second surface of the specimen.

In one embodiment, the illumination system may be configured to illuminate the specimen by scanning a light beam over the specimen. In another embodiment, the illumination system may be configured to illuminate the specimen by scanning a light beam over a wide scan angle on the specimen while the specimen is translated and rotated. In alternative embodiments, the illumination system may be configured to illuminate the specimen with a stationary light beam. In some embodiments, the illumination system may be configured to illuminate the specimen at an oblique angle of incidence. In an alternative embodiment, the illumination system may be configured to illuminate the specimen at a normal angle of incidence.

According to another embodiment, the illumination system may be configured to illuminate the specimen by directing different beams of light to the specimen at different angles of incidence or at different azimuthal angles. In addition or alternatively, the illumination system may be configured to illuminate the specimen by directing different beams of light to one spot on the specimen. The system may be further configured as described herein.

Another embodiment of an inspection system also includes an illumination system configured to illuminate a specimen. The specimen may be a patterned wafer. However, as further described herein, this system may also be configured to inspect both patterned and unpatterned wafers and other specimen. The illumination system may be configured according to any of the embodiments described herein. This embodiment also includes a front detector configured to collect light scattered forwardly from the specimen. In one embodiment, the axis of the front collector may be centered in the plane of incidence at about 60° from normal to about 80° from normal. For example, the axis of the front collector may be centered in the plane of incidence at about 70° from normal. In another embodiment, the front collector may provide a Fourier plane suitable for Fourier filtering of the light collected by the front collector. The system may also include a center collector configured to collect light scattered forwardly and backwardly from the specimen. In addition, the system may include a back collector configured to collect light scattered backwardly from the specimen. Axes of the front, center, and back collectors may be centered in the plane of incidence.

The system further includes a segmented detector. The segmented detector may be configured to separately detect different portions of the light collected by the front collector such that azimuthal and polar angular information about the different portions of the light is preserved. For example, in one embodiment, the system may include a plurality of fibers configured to separately convey the different portions of the light to the detector. The segmented detector may also be configured to produce signals representative of the different portions of the light. In some embodiments, the detector may be an array detector. In other embodiments, the detector may be a multi-anode photo-multiplier tube. Furthermore, the system includes a processor configured to detect defects on the specimen from the signals.

In one embodiment, the system may also include a side collector configured to collect light scattered forwardly from the specimen at different azimuthal angles than the light collected by the front collector. Such an embodiment may also include a side segmented detector. The side segmented detector may be configured to separately detect different portions of the light collected by the side collector such that azimuthal and polar angular information about the light collected by the side collector is preserved. In addition, the side detector may be configured to produce signals representative of the different portions of the light collected by the side collector.

In another embodiment, the system may include a stage, which may be configured to rotate and translate the specimen during inspection. In other embodiments, the stage may be configured to translate the specimen in two lateral directions. In some embodiments, the illumination system may be configured to illuminate a first surface of the specimen. In one such embodiment, the system may also include an optical subsystem configured to detect defects on a second surface of the specimen. For example, the first surface may be a front side of a patterned wafer, and the second surface may be a back side of the patterned wafer. The system may be further configured as described herein.

An additional embodiment relates to an inspection system. The inspection system may be used to inspect patterned or unpatterned wafers. The inspection system includes a stage configured to rotate and translate a specimen. The inspection system also includes an illumination system configured to scan the specimen in a wide scan path during rotation and translation of the specimen. For example, in one embodiment, the wide scan path may be greater than about 0.1 radians. In some embodiments, the illumination system may include an acousto-optical deflector. In addition, the system includes a collector configured to collect light scattered from the specimen. The system further includes a segmented detector configured to separately detect different portions of the light such that angular information about the different portions of the light is preserved. The detector may also be configured to produce signals representative of the different portions of the light. Furthermore, the system may include a processor configured to detect defects on the specimen from the signals.

BRIEF DESCRIPTION OF THE DRAWINGS

Other objects and advantages of the invention will become apparent upon reading the following detailed description and upon reference to the accompanying drawings in which.

Figure 1:
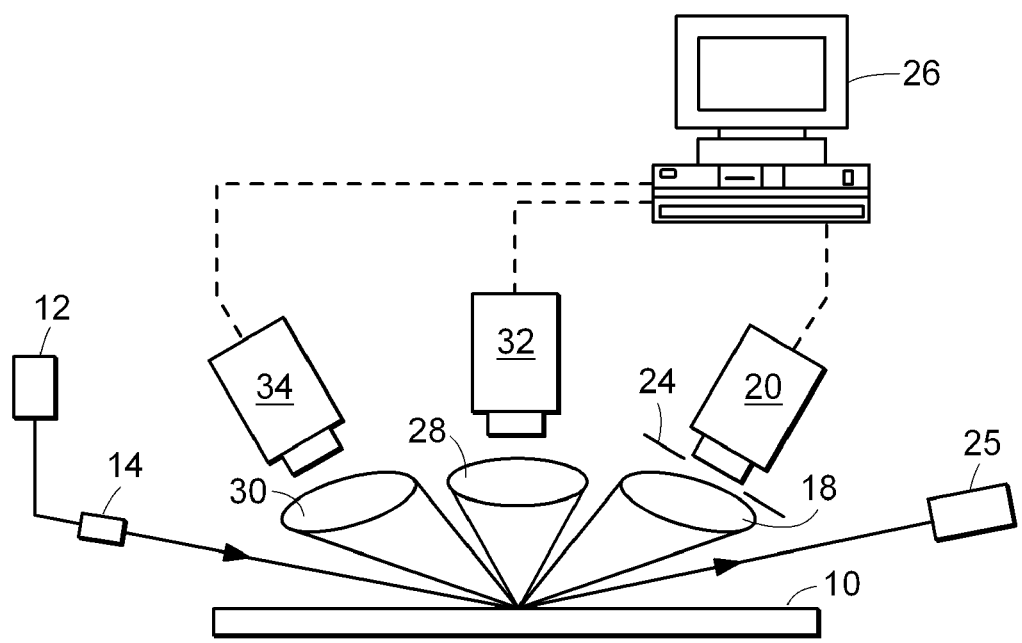
FIG. 1 is a partial schematic diagram of a side view of an embodiment of an inspection system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "defect" generally refers to an abnormality formed on or within a specimen that may adversely affect the performance or functionality of a device formed on the specimen (i.e., reduce a characteristic such as speed or cause a device failure that may or may not cause a device to be non-working) or additional devices formed on the specimen if the cause is not fixed. Defects may be caused by individual process marginalities, process integration marginalities, or interactions between multiple processes. For example, a defect may be contamination on a specimen, abnormal structures on the specimen, damage to the specimen, subsurface pits or crystal originated pits (COPS), subsurface voids, or microscopic scratches. Contamination may include, but is not limited to, particles, fibers, or residual material remaining on a specimen after a process step. Contamination may also include organic or inorganic material such as a resist, a dielectric material, and/or a conductive material. Abnormal structures on a specimen may include, but are not limited to, missing structures, bridging structures, voids formed within structures, structures that have a lateral dimension that is larger than or smaller than a predetermined range of values, and/or structures having an abnormal profile such as roughness, fluting, rounding, and/or a sidewall angle that is larger than or smaller than a predetermined range of values. Damage to the specimen may include, for example, a surface scratch, roughness, breakage of the specimen, or breakage of structures formed on the specimen. As used herein, the term "structures" generally refers to an unpatterned layer of material formed on a specimen, patterned features formed on a specimen, or any combination thereof.

A defect may be present in any location on a specimen. In addition, any number of defects may also be present on the specimen. Furthermore, any number of defects may also be present on any surface of the specimen such as a frontside and/or backside surface of a specimen. A defect may also be microscopic in nature (i.e., not visible to the human eye) or macroscopic in nature (i.e., visible to the human eye).

The term "wafer" generally refers to substrates formed of a semiconductor or a non-semiconductor material. Examples of such a semiconductor or a non-semiconductor material include, but are not limited to, monocrystalline silicon, gallium arsenide, and indium phosphide. Such substrates may be commonly found and/or processed in semiconductor fabrication facilities.

A wafer may include only the substrate such as a virgin wafer or a wafer prior to a first-pass lithography process, which may be commonly referred to as an "unpatterned wafer." Alternatively, a wafer may include one or more layers that may be formed upon a substrate, which may or may not be patterned. For example, such layers may include, but are not limited to, a resist, a dielectric material, and a conductive material. A resist includes any material that may be patterned by an optical lithography technique, an e-beam lithography technique, or an X-ray lithography technique. Examples of a dielectric material include, but are not limited to, silicon dioxide, silicon nitride, silicon oxynitride, and titanium nitride. Additional examples of a dielectric material include "low-k" dielectric materials such as Black Diamond™ which is commercially available from Applied Materials, Inc., Santa Clara, Calif., CORAL™ commercially available from Novellus Systems, Inc., San Jose, Calif., "ultra-low k" dielectric materials such as "xerogels," and "high-k" dielectric materials such as tantalum pentoxide. In addition, examples of a conductive material may include, but are not limited to, aluminum, polysilicon, and copper.

If a layer on the wafer has been patterned, such a wafer is commonly referred to as a "patterned wafer." For example, a patterned wafer may include a plurality of dies having repeatable pattern features. Formation and processing of such layers of material may ultimately result in completed semiconductor devices. As such, a patterned wafer may include a substrate on which not all layers of a complete semiconductor device have been formed or a substrate on which all layers of a complete semiconductor device have been formed.

The specimen may further include at least a portion of a thin-film head die formed on a wafer, at least a portion of a micro-electro-mechanical system (MEMS) device formed on a wafer, flat panel displays, magnetic heads, magnetic and optical storage media, and at least a portion of other components that may include photonics and optoelectronic devices such as lasers, waveguides and other passive components processed on wafers, print heads, and bio-chip devices processed on wafers.

In some cases, the specimen may be a reticle. A "reticle" or a "mask" is generally defined as a substantially transparent substrate having substantially opaque regions formed thereon and configured in a pattern. The substrate may include, for example, a glass material such as quartz. A reticle may be disposed above a resist-covered wafer during an exposure step of a lithography process such that the pattern on the reticle may be transferred to the resist. For example, substantially opaque regions of the reticle may protect underlying regions of the resist from exposure to an energy source.

Although in further description of this embodiment, the term "specimen" is used interchangeably with the term "wafer," it is to be understood that this embodiment and all other embodiments described herein are not limited to wafers and can be performed for any of the other specimens described above.

Turning now to the drawings, it is noted that FIGS. 1–12 are not drawn to scale. In particular, the scale of some of the elements of the figures are greatly exaggerated to emphasize characteristics of the elements. It is also noted that FIGS. 1–12 are not drawn to the same scale. Elements shown in more than one figure that may be similarly configured have been indicated using the same reference numerals.

FIG. 1 is a schematic diagram of a side view of an embodiment of an inspection system. The system may be configured to inspect patterned wafers. The system, however, may also be used to inspect unpatterned wafers or other specimen. The system includes an illumination system configured to illuminate specimen 10. For example, the illumination system includes light source 12. Light source 12 may include, for example, a laser, a diode laser, a helium neon laser, an argon laser, a solid state laser, a frequency doubled YAG laser, a xenon arc lamp, a gas discharging lamp, or an incandescent lamp. The light source may be configured to emit near monochromatic light or broadband light. In addition, the light source may be configured to emit ultraviolet light, visible light, and/or infrared light. Furthermore, the light source may be configured to emit light of various polarizations. The light directed to the specimen may also be coherent or incoherent, but coherent monochromatic illumination may be preferred if the system is to filter out signals from periodic features using Fourier filtering as described herein. The illumination system may also include a number of other components which are not shown in FIG. 1 such as a beam expander, folding mirrors, focusing lenses, cylindrical lenses, beam splitters, spectral filters, polarizing filters, polarizers, and waveplates.

Figure 2:
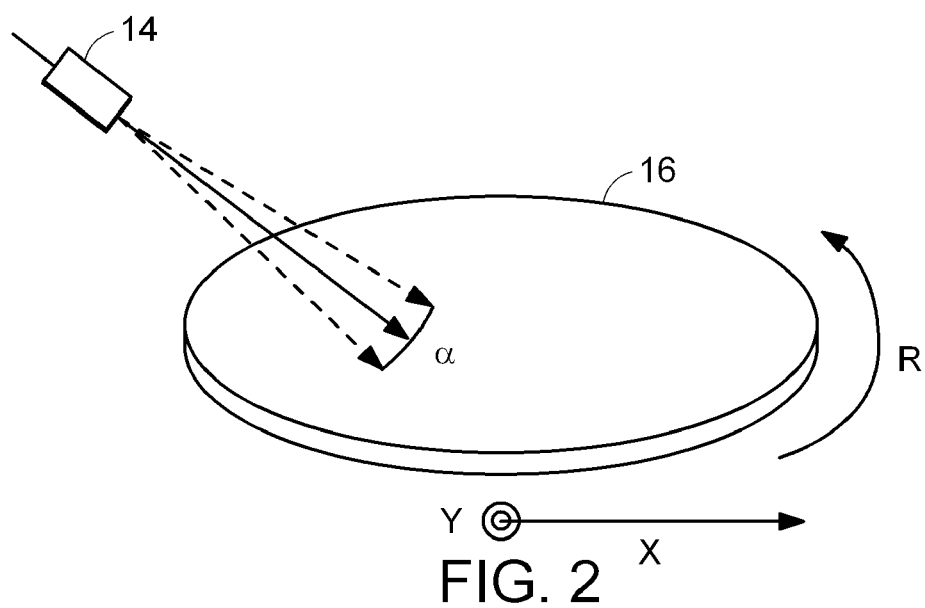
FIG. 2 is a partial schematic diagram of a perspective view of an embodiment of an inspection system, which is configured to scan a light beam over a wide scan angle on a specimen.

The illumination system also includes deflector 14. Deflector 14 may be an acousto-optical deflector (AOD). In other embodiments, the deflector may include a mechanical scanning assembly, an electronic scanner, a rotating mirror, a polygon based scanner, a resonant scanner, a piezoelectric scanner, a galvo mirror, or a galvanometer. The deflector scans the light beam over the specimen. In some embodiments, the deflector may scan the light beam over the specimen at an approximately constant scanning speed. As shown in FIG. 2, deflector 14 may scan the light beam over scan angle α. In some instances, the deflector may scan the light beam over a wide scan angle on the specimen. In one embodiment, the wide scan angle may be greater than about 0.1 radians. An appropriate deflector that can scan a light beam over a wide scan angle includes an acousto-optical deflector that can scan a relatively long line in a relatively short time. The scan angle defines the width of the scan line on the specimen. Therefore, increasing the scan angle increases the width of the scan line, which thereby increases the throughput of the system.

In some embodiments, the illumination system may be configured to perform a telecentric scan of the specimen with a scan lens. For example, the illumination system may be configured such that the scanned beam from the deflector passes through a scan lens thereby resulting in a telecentric scan. In one embodiment, the telecentric scan may have a length that is significantly greater than the spot size of the scanned beam.

The light incident on the specimen may have a relatively small spot size, which may be defined by the full width, half maximum of the spot. In one embodiment, the spot size may have a full width, half maximum of less than 0.1 mm. In some embodiments, the spot size may be less than about 60 µm, preferably less than about 40 µm, and more preferably less than about 30 µm. Illuminating the specimen with a relatively small spot will increase the sensitivity of the system to smaller defects such as smaller particles. In particular, laser power and spot size together determine the power density, which is directly proportional to the scattered signal strength. Furthermore, a small field of view at the specimen plane provides improved edge detection performance.

As further shown in FIG. 2, the system includes stage 16 upon which a specimen may be disposed during inspection. Stage 16 may be configured to rotate the specimen during inspection in the direction indicated by vector R. Stage 16 may also be configured to translate the specimen in the direction indicated by vector Y (as shown into the plane of the paper). The stage may be configured to rotate and translate the specimen at the same time such that the light beam is scanned over the specimen in a spiral-like path. Such a stage may be commonly referred to as an "rθ stage." In some embodiments, the speeds at which the specimen is rotated and translated may be varied during scanning to maintain a substantially constant scanning speed. In other embodiments, the stage may be configured to translate the specimen in two lateral directions X and Y, shown in FIG. 2. This stage may be commonly referred to as an "xy stage." In such embodiments, the stage may be configured to translate the specimen such that the light beam is scanned over the specimen in a serpentine-like path. The stage may include any suitable mechanical or robotic assembly known in the art. In some embodiments, the stage may include an edge handling mechanism. For example, the stage may include mechanical features (not shown) that are configured to contact the edge of the specimen and to support the specimen a spaced distance above the upper surface of the stage. In this manner, cross-contamination of the backside of the specimens may be reduced, and even prevented.

Prior to placing the specimen on the stage, the wafer may be aligned. For example, the inspection system may include an alignment module (not shown). The alignment module may be configured to coarse align the specimen, as opposed to fine alignment or substantially precise alignment. In some embodiments, the alignment module may include an optical subsystem. The optical subsystem may be configured to illuminate the specimen and to detect an alignment mark on the specimen. In some cases, the alignment mark may be a notch, a flat, or some other indentation into the periphery of the wafer. In other cases, the alignment mark may be a permanent identification mark such as a series of alphanumeric characters formed on the specimen. In addition, the alignment mark may include any feature formed on the specimen. Coarse aligning a specimen prior to inspection allows the inspection scan to begin at a predetermined position on the specimen. In addition, scanning of multiple specimen may begin at approximately the same place on each wafer. Furthermore, if the scan begins at a relatively known position on a specimen, the data acquired during scanning may be assigned relative or absolute positions with respect to the alignment mark.

In one embodiment, the inspection system may include a load module (not shown). The load module may be configured to receive and hold one or more specimens. For example, the load module may be configured to receive a single wafer, or more preferably a wafer cassette. In addition, the inspection system may include a specimen handler (not shown) such as a robotic wafer handler or any other specimen handler known in the art. The handler may be configured to remove a specimen from the load module. If pre-alignment is to be performed, the handler may place the specimen in the alignment module. After coarse alignment of the specimen, the handler, or in alternative embodiments a second, different specimen handler, may move the specimen from the alignment module to the stage.

As shown in FIG. 1, the illumination system may be configured to illuminate the specimen at an oblique angle of incidence. In some embodiments, the illumination system may be configured to illuminate the specimen at a relatively low angle of incidence, as measured from the surface of the specimen. For example, the illumination system may be configured to illuminate the specimen at an angle of about 5° to about 30° from the surface of the specimen. The illumination system may also be configured such that the specimen may be illuminated at a selected or variable angle of illumination. For example, the illumination system may include one or more controllers (not shown) that may be configured to alter a position of one or more components of the illumination system such as one or more folding mirrors and the deflector.

The system includes collector 18 that is configured to collect light scattered from the specimen. The axis of collector 18 is centered in the plane of incidence. In addition, the axis of the collector is positioned at about 60° from normal to about 80° from normal. In one example, the axis of the collector may be positioned at about 70° from normal. The position of the axis of the collector with respect to normal, however, may vary depending upon, for example, characteristics of the specimen, the defects of interest, and the angle of incidence of the illumination. In this manner, collector 18 is configured to collect light scattered forwardly from the specimen. Collector 18 is a refractive optical component such as a lens or a compound lens. Alternatively, collector 18 may be replaced by a reflective or partially reflective optical component such as a mirror.

Collector 18 may be configured to collect light scattered forwardly from the specimen over a range of azimuthal angles and a range of polar angles. As used herein, the term "polar angle" is defined as the angle at which light is scattered from the specimen as measured from normal to the surface of the specimen. As used herein, the term "azimuthal angle" is defined as the angle at which light is scattered from the specimen as measured from the plane of incidence. Therefore, collector 18 collects light scattered from the specimen across a two dimensional space.

Figure 4:
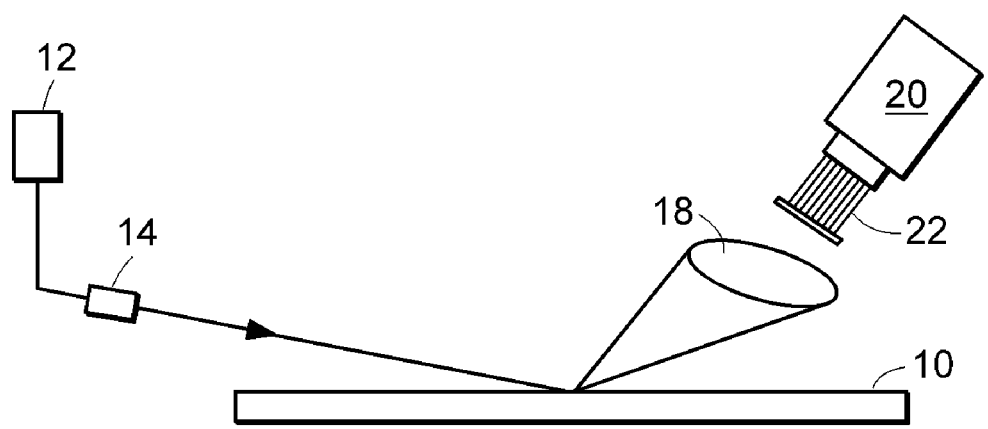
FIG. 4 is a partial schematic diagram of a side view of an embodiment of an inspection system, which includes a plurality of fibers configured to separately convey different portions of light from a collector to a segmented detector.
Figure 5:
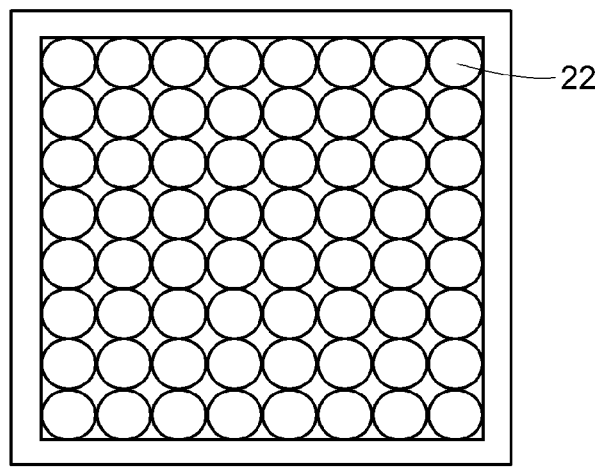
FIG. 5 is a schematic diagram of a cross-sectional view of an embodiment of a plurality of fibers configured as described herein.

The system also includes segmented detector 20. Segmented detector is configured to separately detect different portions of the light collected by collector 18 such that azimuthal and polar angular information about the different portions of the light is preserved. For example, as shown in FIG. 4 in which several other elements of the system have been eliminated for clarity, the system may include plurality of fibers 22. The plurality of fibers may be configured to separately convey the different portions of the light to the detector. For example, as shown in the cross-sectional view of FIG. 5, the fibers may be arranged in a two-dimensional array. Although the fibers are shown in a rectangular array in FIG. 5, it is to be understood that the two-dimensional array of fibers may have other shapes as well. The optically transmissive cores of the fibers located proximate each other in the arrangement shown in FIG. 5 are separated from each other by the claddings that surround the cores thereby reducing cross-talk between the fibers.

Light that is forwardly scattered from the specimen may be incident on a number of the fibers. In some cases, the scattered light may not impinge on each of the fibers. However, since the scattered light will impinge on a number of the fibers, individual fibers will pick up only a portion of the total light collected by the collector. In this manner, each of the fibers on which light impinges will convey a different portion of the light collected by the collector to detector 20. Other optical channels may also be used in place of the optical fibers. Cross-talk between these channels may be reduced by separators such as the claddings that surround optical fibers or other optical separators. In other embodiments, the plurality of fibers may not be included in the system. For example, it is also possible to place individual detectors or segmented detectors in the path of the light collected by the collector rather than using optical fibers or other optical channels.

In one embodiment, the detector may include an array detector such as a charge-coupled device (CCD) camera or a time delay integration (TDI) camera. Other examples of array detectors include a CMOS photodiode or photogate cameras. In another example, the detector may include any detector that has a two-dimensional array of photosensitive elements. In some embodiments, the detector may be a multi-anode photo-multiplier tube. Some cross-talk may be present between adjacent channels of a multi-anode photo-multiplier tube. In such an instance, the plurality of fibers may be aligned with every other anode to reduce such cross-talk. In other embodiments, the detector may be a two-dimensional array of individual detectors. Different photosensitive elements of the detector will detect different portions of the collected light depending on the azimuthal and polar angles of the scattered light. In this manner, the light is detected as a function of the azimuthal and polar angles of the scattered light. As such, the azimuthal and polar angular information about the different portions of the light is preserved by the detector. In one embodiment, the detector may also be configured to produce signals representative of the different portions of the light. In alternative embodiments, the system may include optical or electronic components (not shown) coupled to the detector that can produce signals representative of the different portions of light detected by the detector.

As described above, the illumination system may include a deflector such as an acousto-optical deflector. In addition, the illumination system may be configured such that the light is directed to the specimen at an oblique angle of incidence. Therefore, in such an embodiment, the illuminated spot on the specimen will have an elliptical shape. In some embodiments, this oblique angle of incidence may be very low with respect to the surface of the specimen (i.e., a grazing angle of incidence). In this manner, the illuminated spot on the specimen may have an elliptical shape that has a small width compared to the length of the spot. As such, the illumination system may illuminate an elongated spot on the specimen. In some embodiments, the illumination system may be configured to illuminate an elongated spot on the specimen using in-plane oblique focused line illumination. Examples of the in-plane oblique focused line illumination technique are illustrated in U.S. patent application Ser. No. 08/904,892 by Guoheng Zhao et al., filed on Aug. 1, 1997, which is incorporated by reference as if fully set forth herein. In addition, the deflector may be configured to scan a relatively long line in a relatively short period of time (i.e., a "fast scan" or a "fast AOD").

In one such embodiment, the inspection system may include a streak camera (not shown). A streak camera is a device that can measure ultra-fast light phenomena and can deliver intensity vs. time vs. position information. The streak camera is a two-dimensional device that can be used to detect several tens of light channels simultaneously. Generally, during operation of the streak camera, light being measured passes through a slit and is formed by the optics into a slit image on a photocathode of the streak tube. The incident light on the photocathode is converted into a number of electrons proportional to the intensity of the light. The electrons pass through a pair of accelerating electrodes, where they are accelerated against a phosphor screen. On the phosphor screen, the vertical direction serves as the time axis. In addition, the position in the horizontal direction of the phosphor image corresponds to the horizontal location of the incident light. The brightness of the various phosphor images is proportional to the intensity of the respective incident optical pulses. In this manner, the streak camera can be used to convert changes in the temporal and spatial light intensity being measured into an image showing the brightness distribution on the phosphor screen. As such, the optical intensity and the incident light time and position may be determined from the phosphor image. Streak cameras are commercially available from Hamamatsu Photonics K.K., Systems Division, Japan.

In one embodiment, the horizontal direction of the phosphor screen, or the direction that corresponds to spatial position of the incident light, may be positioned to correspond to the length of the elliptical illuminated spot on the specimen. In this manner, the streak camera may measure the intensity of the light reflected from different positions across the illuminated spot in a direction perpendicular to the scan direction. In addition, the vertical direction of the phosphor screen, or the direction that corresponds to time of the incident light, may be positioned to correspond to the width of the elliptical illuminated spot on the specimen. As such, the streak camera may measure the intensity of light reflected from the different positions across the illuminated spot as a function of time or as the light is scanned over the specimen. The streak images formed on the phosphor screen may be used to form darkfield images of the specimen.

In another embodiment, the inspection system may include a plurality of fibers, which may be configured as described above. The plurality of fibers may be configured to separately convey different portions of the light collected by the collector to different positions across the slit of the streak camera. In some embodiments, the plurality of fibers may be arranged in a one-dimensional array proximate the slit of the streak camera. As described above, the plurality of fibers may be arranged in a two-dimensional array proximate the collector. Therefore, in some embodiments, the plurality of fibers may convey light collected across a two-dimensional space to a one-dimensional array across the streak camera. In a different embodiment, the plurality of fibers may be arranged in a one-dimensional array proximate the collector. In such an embodiment, therefore, the plurality of fibers may convey light collected across a one-dimensional space to a one-dimensional array across the streak camera. In either embodiment, however, the plurality of fibers and the streak camera will preserve the spatial information (i.e., azimuthal and/or polar angular information) about the collected light.

The phosphor screen described above is on the output side of the streak camera. An array detector is coupled to the output side of the camera to read the streak images produced on the phosphor screen. In one embodiment, a CCD camera may be used to read the images from the phosphor screens of streak cameras. Such a camera may be preferable because the streak image is faint and disappears in an instant. Therefore, such a high-sensitivity camera is preferably used. The streak images may be transferred through a frame grabber board to a processor for analysis as described herein.

In some embodiments, collector 18 may provide Fourier plane 24 suitable for Fourier filtering of the collected light. In one embodiment, the collector may be a reasonably good lens such as a lens that is not well corrected and does not have relatively good imaging quality. For example, the collector may provide a relatively high-quality pupil plane for Fourier filtering, which may be used to detect defects on a specimen having a regularly repeating pattern upon its surface such as an array of structures on a semiconductor wafer. Generally, repeating patterns on the surface of the specimen cause the light to diffract in approximately uniform angles at regularly spaced intervals. Preferably, the Fourier plane has relatively good image quality, is relatively flat, and is relatively distortion free such that the image will contain small diffraction spots from the repeating periodic structures on the surface.

In one embodiment, Fourier filtering may be accomplished by inserting a mechanical Fourier filter (not shown) into the Fourier plane. Examples of optical Fourier filters include liquid crystal display (LCD)-based filters and photographic-based filters. Additional examples of optical Fourier filters are illustrated in U.S. Pat. No. 5,970,168 to Montesanto et al. and U.S. Pat. No. 6,020,957 to Rosengaus et al., which are incorporated by reference as if fully set forth herein. Therefore, by blocking out the diffraction spots from the repeating periodic structures on the surface of the specimen, only randomly scattered light will pass through the Fourier plane and on to the detector. Detection of the randomly scattered light may be used to detect defects on the specimen since defects in the specimen cause the light to scatter randomly and very little of their signal will be blocked by the Fourier filter. In this manner, the system may be configured to cancel signals from patterned features on the specimen, or to perform periodic feature elimination (PFE), optically. In addition, the system may be configured to perform two-dimensional periodic feature elimination (2DPFE) optically (i.e., to cancel signals from features on the specimen in two-dimensions optically). For example, the optical Fourier filter may be configured to block diffractions spot from repeating periodic structures on the surface of the specimen in two-dimensions.

In another embodiment, all of the collected light may be allowed to reach the detector. In such an embodiment, the light diffracted by the repeating periodic structures may be relatively intense compared to the light randomly scattered from the specimen. In some instances, light diffracted by repeating periodic structures may saturate the segments of the detector upon which it impinges. In contrast, other segments of the detector that detect only randomly scattered light from the specimen will provide useful signals for defect detection. In this manner, the different portions of the scattered light that contain light diffracted from the repeating periodic structures may be identified. In addition, the signals representative of these different portions of the scattered light may be discarded and not used to detect defects on the specimen. The signals representative of light diffracted from periodic structures may be identified as the signals are received.

When the system is used for inspecting wafers with memory cells thereon (i.e., "array wafers"), the Fourier components from the memory array will spin as the wafer is rotated. These components will, therefore, rotate and be at different azimuthal angles about the normal direction. As such, these Fourier components will be conveyed to different segments of the detector as the wafer is rotated. Since the array of memory cells may have different dimensions in the x and y directions of the wafer, as the wafer rotates, the number of detectors that are saturated by the Fourier components will change. The number of detectors that will be saturated can be determined from the x and y dimensions of the memory cells such that the number of Fourier diffraction components can be estimated.

Alternatively, during initialization of the system, the specimen may be scanned, and the number of different portions of the light that contain light diffracted from periodic structures may be obtained. For example, the number of detector segments that contain Fourier components may be determined by recording the number of detector segments with relatively strong, or saturated, output signals. During inspection of the specimen, this number of signals having the highest intensities may be discarded. In some cases, the signals from detector segments adjacent to the segments containing Fourier components may also be discarded to reduce cross-talk. In this manner, the system may be configured to cancel signals from features on the specimen, or to perform periodic feature elimination (PFE), electronically. In addition, the system may be configured to perform two-dimensional periodic feature elimination (2DPFE) electronically (i.e., to cancel signals from features on the specimen in two-dimensions electronically). For example, the processor may be configured to determine which signals from individual detector segments contain light diffracted from repeating periodic structures on the surface of the specimen in two-dimensions. Further examples of Fourier filtering are illustrated in U.S. Pat. No. 6,288,780 B1 to Fairley et al., which is incorporated by reference as if fully set forth herein. Additional examples of inspection of array wafers are illustrated in U.S. Pat. No. 6,538,730 B2 to Vaez-Iravani et al., which is incorporated by reference as if fully set forth herein.

In addition, the detector may be selected or designed such that at least some of the photosensitive elements or segments produce signals that do not contain Fourier components of the scattered light. For example, if the number of segments in the detector is relatively low, the probability that all of the segments will receive Fourier components of the scattered light may be relatively high. Therefore, the number of segments of the detector may be increased sufficiently such that at least some of the segments do not receive the Fourier components. Additional examples on how to design a segmented detector such that not all of the segments receive Fourier components are illustrated in U.S. Pat. No. 6,538, 730 B2 to Vaez-Iravani et al., which is incorporated by reference as if fully set forth herein.

If the collector has a relatively high numerical aperture (NA), the amount of light collected by the collector that ultimately reaches the detector may be adjusted based on various specimen characteristics. For example, the collector may have a relatively high NA such that the collector may collect light scattered over an angular range of about 60° to about 90°. In one such embodiment, the system may also include a collection diaphragm (not shown) or another optical component having an adjustable aperture. The collection diaphragm or another suitable optical component may be disposed between the collector and the segmented detector. Adjusting the aperture alters the amount of light collected by the collector that reaches the detector. In addition, the aperture may be adjusted to alter which azimuthal and polar angles at which light is detected. For example, the aperture may be adjusted such that the detector may detect light collected by the collector and scattered from polar angles relatively close to the wafer (e.g., about 5° from the surface to about 30° from the surface) or scattered at polar angles relatively close to normal (i.e., about 0° from normal to about 30° from normal). The aperture may be adjusted based on characteristics of the specimen such as roughness and haze. For example, the aperture may be adjusted such that light scattered due to roughness and/or haze is not detected by the segmented detector.

In some embodiments, the inspection system may also be configured to detect light specularly reflected from the specimen. The specularly reflected light may be collected and detected separately from the scattered light. For example, in one embodiment, the system may include bright field detector 25. Bright field detector 25 may be configured to detect light specularly reflected from the specimen. In some embodiments, the bright field detector may be configured to form an image of the specimen. Examples of appropriate bright field detectors include, but are not limited to, a photo-multiplier tube, a photodiode, a quadrant-cell device, a CCD camera, and a TDI camera. In addition, the inspection system may include various other components (not shown) optically coupled to the bright field detector such as one or more lenses and a beamsplitter.

As shown in FIG. 1, the system also includes processor 26. Processor 26 may be configured to detect defects on the specimen from the signals or data produced by the detector or other electronic components coupled thereto. In some embodiments, the processor may store the signals or data such that the processor may perform a number of functions on the signals or the data. For example, the processor may include some type of memory medium suitable for the storage of such signals or data. In one embodiment, the processor may be configured to store signals or data corresponding to at least several tracks on the specimen, where a track is generally defined as the scan path on the specimen in which data was acquired. Alternatively, the processor may process the signals or data without, or prior to, storing the signals or the data. The processor may perform a number of functions on the signals or data depending on, for example, the type of specimen being inspected or the defects of interest.

In one embodiment, the processor may perform one-dimensional filtering (1D filtering) of the signals or data. Performing 1D filtering may include using one or more algorithms to search a track of data for periodicity or other repetitive characteristics of the signals or the data in the track. In another embodiment, the processor may perform 2D filtering of the signals or the data. Performing two-dimensional (2D filtering) may include using one or more algorithms to search multiple tracks of data (i.e., one track of data and points on either side of the track) for periodicity or other repetitive characteristics of the signals or the data in the multiple tracks. Such 2D filtering may provide more local information for regions of the specimen in which defects are being detected. In some embodiments, the processor may also perform segmentation and reconstruction of the data or the signals. For example, based on 1D filtering, 2D filtering, or other pattern recognition algorithms, the processor may separate portions of a track that are associated with different die, cells, or other groups of repetitive patterned features on the specimen. The processor may also separate portions of multiple tracks on the wafer in this manner. In addition, the processor may combine separated portions of multiple tracks that are associated with the same die, cells, or other groups of repetitive patterned features on the specimen. In this manner, the processor may segment tracks of data and reconstruct the data into meaningful groups. Reconstructed data may then be further processed or analyzed.

In another embodiment, the processor may perform thresholding of the signals or the data. For example, thresholding may include comparing the signals or the data to a first threshold. This comparison may be used to identify signals or data that contain Fourier components of scattering from periodic or other repetitive structures on the specimen. For example, if the signals or the data are greater than the first threshold, the signals or the data may be identified as containing such Fourier components and may be discarded or otherwise not used for defect detection. Thresholding may also include comparing the signals or the data to a second threshold. This comparison may be used to identify signals or data that contain background scatter or other noise. For example, if the signals or the data are less than the second threshold, these signals or data may also be identified as containing background scatter or noise and may also discarded or otherwise not used for defect detection. The signals or data that are both below the first threshold and above the second threshold may then be further analyzed for defect detection.

In some embodiments, the processor may also be configured to perform 2 segment Segment Automated Thresholding™, or SAT™. SAT™ involves automatically separating a digitized image of a specimen into different regions called "segments" based on process noise and brightness. Peak sensitivity may be achieved by assigning separate thresholds to each segment of the image rather than a single threshold for the entire image. Optimal thresholds may be automatically determined for each segment based upon the process variability which may exist on the inspected specimen. Being thus able to adapt to changing process conditions may provide greater sensitivity, which may be achieved and maintained wafer-to-wafer and lot-to-lot.

2 segment SAT™ uses high sensitivity in the extreme upper left corner of the mean/range histogram where the mean and range are low. This area is associated with small defects on a background, where the goal is to optimize the sensitivity in the clear areas and evaluate any information available in the rest of the image. After thresholding the data or signals may be reconstructed for further processing or analysis.

Azimuthal filtering generally refers to the identification and rejection of scatter from features on the specimen such as Manhattan geometry (straight line geometry parallel to rectangular die edges), which changes as the azimuthal angle between the scanned beam and a lateral edge of the features changes. If the specimen is scanned in two lateral directions during inspection, one method for reducing the scattering from such features is to arrange the plane of incidence at an azimuthal angle of, for example, about 45° or about 22.5° with respect to the edges of the features. In this manner, scattering from such features will not be collected by the collector. However, as the numerical aperture of the collector increases (i.e., to greater than about 0.7), the amount of scattering from such features that is collected may increase thereby rendering the scattering non-negligible. In addition, scattering from such features will change as the specimen is rotated and translated and as the azimuthal angle between the plane of incidence and the edge of such features changes. Therefore, if the numerical aperture of the collector is relatively large or if the specimen is rotated and translated during inspection, the processor may be configured to perform azimuthal filtering of the signals or the data. For example, azimuthal filtering of the data or the signals may be performed by the processor using the thresholding technique described above. In such an embodiment, the first threshold may be selected such that comparing the signals or data to the first threshold will identify and eliminate signals from such features. In another embodiment, the processor may be configured to perform Fourier filtering as described above. Since features such as Manhattan geometry on a specimen may also be repeatable and may have a predictable period, the Fourier filtering algorithms or mechanisms may be designed such that scatter from such features is also identified and eliminated during Fourier filtering.

In another embodiment, the processor may transform the data from one coordinate system into another coordinate system. For example, if the specimen is scanned while the specimen is rotated and translated, the coordinates of the signals or data may be in "rθ format" or radial and azimuthal coordinates. In such an instance, the processor may be configured to translate the coordinates into "xy format" or Cartesian coordinates. Such transformation of the data or signals may facilitate analysis of the data or signals. For example, the data or signals may be easily associated with particular die or particular features in die when the data or signals are in xy format since the layout of the die and features on a wafer are often laid out in this manner. However, such a transformation is not required.

In yet another embodiment, the processor may receive images from the detector or other electronic components coupled to the detector and the processor. The images may be analog images. The processor may also re-sample the images to alter the orientation of the images. For example, if the images are to be compared with other images such as a reference image or another image generated by inspection, they need to be brought into registration with each other. Therefore, the processor may re-sample the images such that they are aligned to the reference image or the other images for image subtraction or other processing. If two images generated by inspection are to be compared, each of the two images may be re-sampled to half of the registration difference between them such that each image is degraded by the re-sampling process by the same amount thereby keeping the eventual processing of the two images approximately the same.

In an additional embodiment, the processor may detect defects on a specimen by comparing signals or data corresponding to one die on the specimen to signals or data corresponding to another die on the specimen. For example, two images representing different die on a specimen may be subtracted from one another. The processor may also compare the image subtraction difference to a predetermined threshold. An image subtraction difference that is greater than the threshold may indicate the presence of a defect while an image subtraction difference that is less than the threshold may indicate the absence of a defect. In this manner, signals representing the same location in the die that are different may be identified as possible defects. Such a defect detection method is commonly referred to as "die:die inspection." In some embodiments, the processor may be configured to detect defects on the specimen by comparing signals or data corresponding to one portion of the specimen to signals or data corresponding to a portion of a different specimen. The processor may perform such defect detection in a manner similar to that of die:die inspection. Such a defect detection method is commonly referred to as "wafer: wafer inspection."

In another embodiment, the processor may analyze the data or the signals by die stacking. Die stacking generally involves transferring data representative of a multiple die on a wafer or on multiple wafers to a single 2D map that represents the size of a single die. In this manner, data representing individual die may be overlaid. Data representing defects or other structures that are present in the same location in each or more than one of the overlaid die will appear brighter or darker (depending on the type of map that is generated) in the 2D map than defects or other structures that are not present in the same location in each or more than one of the overlaid die. As such, die stacking may be used to identify defects that are present in approximately the same location in multiple die, defects that are not present in approximately the same location in multiple die, and other, possibly non-periodic or -repetitive, structures that are present in approximately the same location in multiple die which are not defects. In some embodiments, the processor may analyze the data or the signals by wafer stacking, which may be performed as described above.

The processor may also be configured to perform any of the methods illustrated in U.S. Pat. No. 6,021,214 to Evans et al., which is incorporated by reference as if fully set forth herein. The processor may also be further configured as described by Evans.

As further shown in FIG. 1, the inspection system may include more than one collector. In such an embodiment, collector 18 may be referred to as a "front collector" since it is arranged to collect light scattered forwardly from the specimen. The inspection system may also include center collector 28. Center collector 28 may be configured to collect light scattered forwardly and backwardly from the specimen. The center collector may collect light scattered forwardly from the specimen at polar angles closer to normal than the front collector. In addition, the system may include back collector 30. Back collector 30 may be configured to collect light scattered backwardly from the specimen. The back collector may be configured to collect light scattered backwardly from the specimen at polar angles farther from normal than the center collector. The center and/or the back collectors are refractive optical components such as lenses or compound lenses. Alternatively, the center and/or the back collectors may be replaced by reflective optical components such as mirrors. Although the embodiment illustrated in FIG. 1 includes both a center and a back collector, it is to be understood that the system may also include only one of the collectors in addition to the front collector.

Furthermore, the system may also include a collection diaphragm (not shown) or another suitable optical component disposed between each of the collectors and a detector. The collection diaphragm or other optical component may be configured as described above. In this manner, the overall amount of light collected by each collector that reaches each detector may be adjusted independently. In addition, although each collector may collect some light during inspection of a specimen, the signals that correspond to the collected light that are used for defect detection may selected based on the specimen characteristics. For example, in one instance, signals produced by detectors coupled to the front and back collectors, but not signals produced by a detector coupled to the center collector, may be used for defect detection. In another example, signals produced by a detector coupled to only one of the collectors may be used for defect detection.

Figure 3:
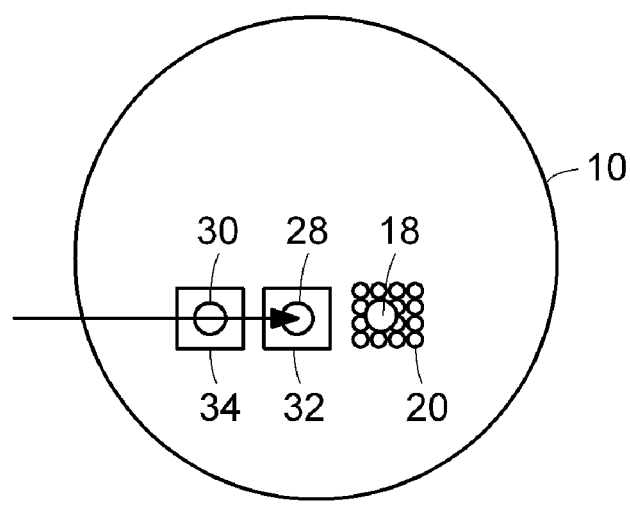
FIG. 3 is a partial schematic diagram of a top view of the embodiment illustrated in FIG. 1.

In one embodiment, the three collectors may be arranged such that the axis of each collector is centered in the plane of incidence, as shown in the partial schematic diagram of a top view of the system illustrated in FIG. 3. In this manner, the collection optics of the inspection system may be symmetrical about the plane of incidence. In addition, although each collector is configured to collect light scattered from the specimen at different polar angles, each collector may be configured to collect light scattered from the surface of the specimen at the same azimuthal angles. As such, the collectors may be configured in an angular symmetric optical arrangement. In another embodiment, an axis of the center collector may be centered at normal. However, the position of the axis of the center collector may be offset from normal depending on, for instance, characteristics of the specimen or defects of interest. The axis of the back collector may also vary greatly and, in some embodiments, may be positioned at about 35° from normal to about 70° from normal.

The system may further include more than one detector. Each detector may be coupled to one of the collectors. As described above, detector 20 that is configured to collect light from the front collector is a segmented detector. Detectors 32 and 34 that are configured to detect light from the center collector and the back collector, respectively, may not be segmented. In this manner, the detectors coupled to the center and back collectors may produce one signal that is representative of the scattered radiation that is collected by the respective collectors. One example of such detectors is a single-anode photo-multiplier tube. Alternatively, the detectors that are arranged to detect light from the center collector and/or the back collector may be segmented. These detectors may be configured as described further herein. In such an embodiment, the center collector and/or the back collector may be configured to provide a Fourier plane (not shown) suitable for Fourier filtering of the collected light as described above.

In alternative embodiments, the front, center, and back collectors may be replaced by a single collector that can collect light scattered both forwardly and backwardly at relatively large angles with respect to normal. For example, the single collector may be configured to collect light scattered at about 60° with respect to normal to about 80° with respect to normal, or in one example at about 70° with respect to normal, at any azimuthal angle. In one embodiment, a large lens that has a relatively large numerical aperture may be configured to collect light across a broad range of azimuthal and polar angles, both forwardly and backwardly. In another embodiment, the single collector may be replaced by a reflective optical component such as a mirror that has some degree of curvature, which may also be configured to collect light across a relatively broad range of azimuthal and polar angles, both forwardly and backwardly. The system may also include a collection diaphragm (not shown) or another suitable optical component disposed between the single collector and a segmented detector. The collection diaphragm or other optical component may be configured as described above. For example, the single collector may preferably provide a Fourier plane (not shown) such that Fourier filtering of the collected light may be performed as described above. In this manner, the Fourier components of the scattered light may be identified and eliminated as described herein prior to defect detection.

One or more detectors may also be coupled to the single collector. Each of the detectors may be configured to detect different portions of the light collected by the single collector. For example, each of the detectors may be arranged such that each of the detectors detects light over a different solid angle, depending upon the elevational and azimuthal angle of the detectors. At least one of the detectors may be a segmented detector. In addition, all of the detectors may be segmented detectors. This embodiment may be further configured as described herein.

In a further embodiment, the collectors described above may be arranged with respect to the illumination system in a double-darkfield arrangement. For example, the illumination system may be configured to illuminate the system with relatively low angle (darkfield) illumination. In addition, any of the collectors described herein may be configured as relatively low angle collection optics. In this manner, the system may be suitable for detection of various types of defects such as particulate contamination, microscratches, and planar defects at relatively high throughput.

In yet another embodiment, any of the embodiments described herein may be modified such that a first portion of the light collected by a collector may be directed to a non-segmented detector while a second portion of light collected by the collector may be directed to a segmented detector. For example, a beamsplitter (not shown) may be disposed between the front collector and the segmented detector. The beamsplitter may allow a portion of the light collected by the front detector to reach the segmented detector. The beamsplitter may direct another portion of the light collected by the front detector to another detector (not shown). The additional detector may be a non-segmented detector. Signals produced by the segmented detector may be used to detect defects on patterned wafers. In contrast, signals produced by the non-segmented detector may be used to detect defects on unpatterned wafers. In this manner, light collected by any of the collectors may be directed to both a segmented detector and a non-segmented detector. Consequently, the system may be used for patterned wafer inspection and for unpatterned wafer inspection.

Each of the embodiments described herein may also be further configured as described in U.S. patent application Ser. No. 10/315,340 entitled "Darkfield Inspection System Having Photodetector Array," filed Dec. 9, 2002, which is incorporated by reference as if fully set forth herein. Each of the embodiments described herein may also include any of the components described in this patent application.

In an additional embodiment, the inspection systems described herein may be used for material identification of a defect such as a particle or other contamination on the specimen. For example, in one such embodiment, the light source may be configured to emit p-polarized light or light having a strong p-polarized component. Alternatively, the illumination system may include a polarizing filter, polarizer, or one or more waveplates disposed between the light source and the specimen. The polarizing filter or polarizer may be configured to alter light emitted from the light source such that p-polarized light or light having a strong p-polarized component is incident on the specimen. In such an embodiment, the light is preferably directed at the specimen at an oblique angle of incidence.

Additionally, in such an embodiment, at least forwardly and backwardly scattered light are collected from the specimen. The intensities of the forwardly scattered and backwardly scattered light are measured by the respectively positioned detectors, which produce a signal representative of these intensities. The intensities may be measured by a non-segmented detector as described above. In alternative embodiments, the intensities may be measured by a segmented detector and the intensity across the detector may be determined from the intensity detected by each segment of the detector. To determine the defect material, the processor may compare the forwardly scattered intensity signal and the backwardly scattered intensity signal with a plurality of predetermined scatter patterns. The predetermined scatter patterns may be defined by magnitudes of the forwardly scattered intensity signals and the backwardly scattered intensity signals for a plurality of known materials. Scattering patterns for a number of different defect sizes and materials may be determined using theoretical calculations performed with a scattering model. One scattering model that may be employed is based on the discrete sources method, which has been experimentally verified as is known in the art.

For example, in one embodiment, a ratio of the magnitude of the backwardly scattered intensity signals to the magnitude of the forwardly scattered intensity signals may be determined. This ratio and the magnitude of the backwardly scattered intensity signal may be compared to correlations of the ratio versus the backwardly scattered intensity signal for a plurality of known materials. The defect material may be identified as the known material having a correlation that is closest to the ratio and the backwardly scattered intensity signal of the defect.

In another embodiment, at least backwardly and forwardly and backwardly (i.e., light collected by the center collector) scattered light are collected from the specimen, and the intensities are measured as described above. A ratio of the magnitude of the backwardly scattered intensity signal to the magnitude of the forwardly and backwardly scattered intensity signal may be determined. This ratio and the magnitude of the backwardly scattered intensity signal may be compared to correlations of this ratio versus the backwardly scattered intensity signal for a plurality of known materials. The defect material may be identified as the known material having a correlation that is closest to the ratio and the backwardly scattered intensity signal of the defect.

In some embodiments, the processor may also be configured to determine a size, or a lateral dimension, of the defect. For example, the processor may be configured to determine an average lateral dimension of the defect by comparing a correlation between defect material, lateral dimension, and backwardly scattered intensity signal magnitude to the measured backwardly scattered intensity signal magnitude. In some instances, this determination may be made with the forwardly scattered intensity signal magnitude as opposed to the backwardly scattered intensity signal magnitude. For example, the forwardly scattered intensity signal may provide a more accurate measure of defect size for defects that are greater than about 100 nm. In this manner, the defect size is determined by taking into account the material effects on light scattering intensity thereby providing a more accurate estimation of defect size.

In an additional embodiment, the inspection systems described herein may be used to determine if a defect is located on the surface of the specimen (i.e., a "surface defect") or if the defect is located partially or entirely below the surface of the specimen (i.e., a "subsurface defect"). One example of a surface defect is a particle or other contamination. Examples of subsurface defects include, but are not limited to, pits, voids, and microscopic scratches. In one such embodiment, the illumination system may be configured to direct a first beam of p-polarized light to the specimen at a first incident angle. The inspection system may detect light scattered from the specimen as described herein and may produce first signals that are representative of the intensities of the scattered light integrated over the collection area. In addition, the illumination system may be configured to direct a second beam of p-polarized light to the specimen at a second incident angle. The second incident angle is greater than the first incident angle, where incident angle is measured from the surface normal. The inspection system may also detect light scattered from the specimen as described herein and may produce second signals that are representative of the intensities of the scattered light integrated over the collection area. If the second signals are greater than the first signals, the defect may be characterized as a surface defect. If the second signals are less than the first signals, the defect may be characterized as a subsurface defect.

In another embodiment, surface defects may be distinguished from subsurface defects by comparing the intensity of p-polarized light scattered from the specimen to the intensity of s-polarized light scattered from the specimen. For example, the inspection system may be configured to direct p-polarized light at the specimen. The p-polarized light scattered from the specimen may be detected as described herein, and the detectors may produce first signals that are representative of the intensities of the p-polarized scattered light integrated over the collection area. The inspection system may also be configured to direct s-polarized light at the specimen. The s-polarized light scattered from the specimen may be detected as described herein, and the detectors may produce second signals that are representative of the intensities of the s-polarized scattered light integrated over the collection area. A ratio of the first signals to the second signals may then be determined by the processor. The ratio may be compared to a predetermined value. If the ratio is greater than the predetermined value, the defect may be identified as a surface defect. If the ratio is less than the predetermined value, the defect may be identified as a subsurface defect.

In the embodiment described above, the illumination system may be configured to illuminate the specimen with one beam of light and to alter the polarization of the beam of light from p-polarization to s-polarization or vice versa between scans. In another embodiment, the illumination system may include two light sources. One light source may emit p-polarized light while the other light source may emit s-polarized light. In one such embodiment, the light source which illuminates the specimen may be switched between scans. In a different embodiment, both light sources may illuminate the specimen. In such an embodiment, two different collectors may collect light scattered from the specimen. One collector may be configured to collect only p-polarized light while the other collector may be configured to collect only s-polarized light. In yet another embodiment, a light source that emits light, which contains both p-polarized and s-polarized components, may be used to illuminate the specimen. Such an inspection system may include two different collectors, each of which collect only s-polarized light or p-polarized light scattered from the specimen.

In a different embodiment, the inspection system may be used to distinguish surface defects from subsurface defects based on detected differences in the angular distribution of the scattered light. In such an embodiment, the illumination system may be configured to illuminate the specimen at one angle of incidence. In addition, the illumination system may be configured to illuminate the specimen with p-polarized light. The processor may be configured to determine differences in the angular distribution of the scattered light by, for example, comparing the amount of the light collected by the center collector to the amount of light collected by the back collector. If a defect is a subsurface defect, the amount of light collected by the center collector will typically be greater than that detected by the back collector. This scattering distribution is particularly characteristic of relatively small subsurface defects (e.g., subsurface defects having a lateral dimension less than about 300 nm). In this manner, if the ratio of the intensity of the light collected by the center collector to the intensity of the light collected by the forward or back collector is more than a predetermined value, the defect may be classified as a subsurface defect. On the other hand, if the defect is a surface defect, the amount of light collected by the center collector will typically be less than that detected by the back collector and/or the front collector. Therefore, if the ratio of the intensity of the light collected by the center collector to the intensity of the light collected by back collector is less than a predetermined value, the defect may be classified as a surface defect. In addition, the intensity of the light collected by the individual collectors may be indicative of the size of the subsurface or surface defects. Additional examples of methods for distinguishing between particles and micro-scratches is illustrated in International Application Number PCT/IUS02/10783 (Publication No. WO 02/082064 A1) by Vaez-Iravani et al., which is incorporated by reference as if fully set forth herein.

Figure 13:
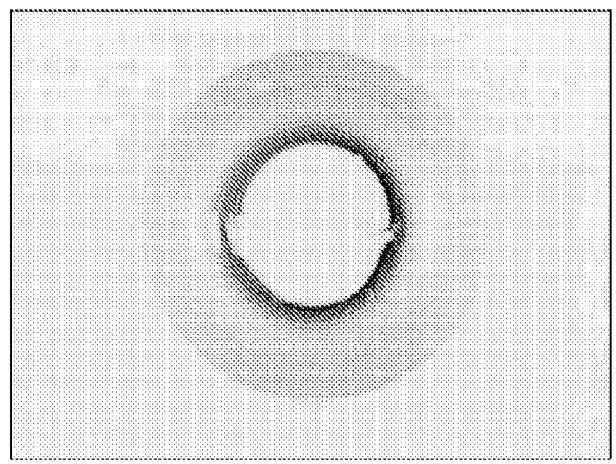
FIGS. 13–18 are measured scattering patterns produced by illuminating defects having different shapes and different orientations of the major axes.
Figure 14:
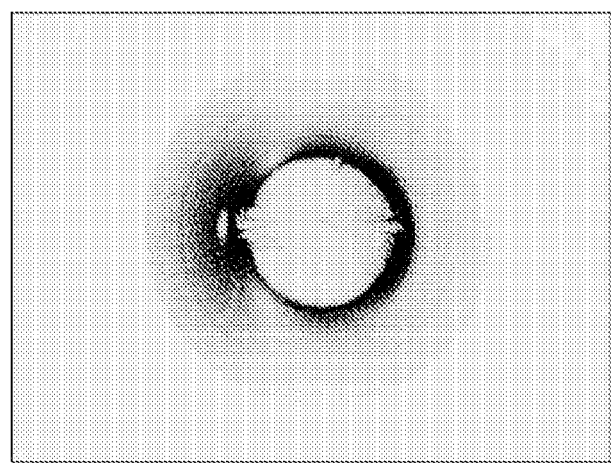
Figure 15:
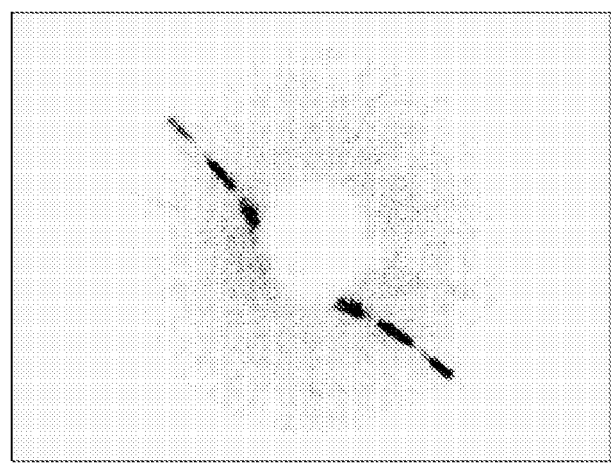
Figure 16:
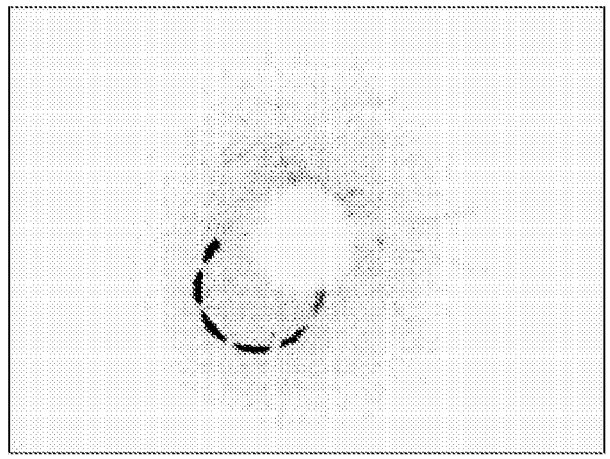

In another embodiment, classification of defects may be based on shape and/or orientation in addition to, or as an alternative to, material, size, and location (i.e., surface or subsurface). For example, defects that are elongated (i.e., scratches, slip lines, etc.) will have characteristic (elongated) scattering patterns in the Fourier plane. Scattering patterns of different types of defects are illustrated in FIGS. 13–16. FIG. 13 is a measured scattering pattern produced by illuminating a 496 nm polystyrene latex sphere with P-U polarized light at a normal angle of incidence. FIG. 14 is a measured scattering pattern produced by illuminating a 496 polystyrene latex sphere with P-U polarized light at an oblique angle of incidence. FIG. 15 is a measured scattering pattern produced by illuminating a scratch on an aluminum wafer at a normal angle of incidence. FIG. 16 is a measured scattering pattern produced by illuminating the scratch with P-U polarized light at an oblique angle of incidence.

As shown in FIGS. 13–16, scratches produce scattering patterns that can be differentiated from scattering patterns produced by other defects such as particles. In general, defects that have different shapes will produce different scattering patterns. Therefore, defects having different shapes may be distinguished from one another based on the scattering patterns that they produce. In this manner, scratches, slip lines, other elongated defects, or any other defect that has a characteristic shape may be classified as such based on the scattering patterns produced by the defects.

Figure 17:
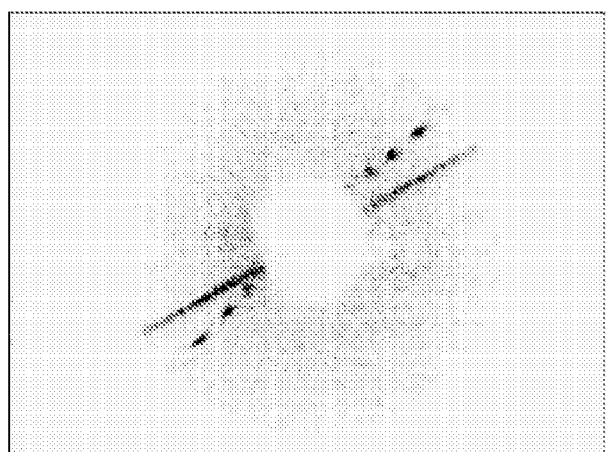
Figure 18:
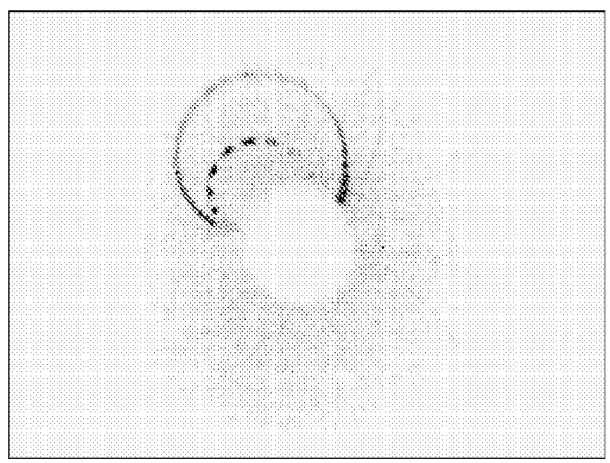

In addition, the orientation of the scattering patterns reflects the orientation of the major axis of the defect. For example, FIGS. 15–18 illustrate scattering patterns produced by scratches having different orientations of their major axes. FIG. 17 is a measured scattering pattern produced by illuminating two scratches on an aluminum wafer at a normal angle of incidence. One of the scratches has a broken pattern, and the other scratch has a continuous or smooth pattern. FIG. 18 is a measured scattering pattern produced by illuminating the two scratches with P-U polarized light at an oblique angle of incidence. As shown in FIGS. 15–18, the scattering pattern produced by a scratch depends on the orientation of the major axis of the scratch. In this manner, scratches or other elongated defects having different orientations of their major axes may be differentiated from one another based on the scattering patterns that they produce. In addition, identifying the major axis of a scratch or another defect may aid in identifying the cause of the defect.

In the above embodiments, identifying the defect material, determining the defect size and/or distinguishing between subsurface and surface defects may be performed for each detected defect. In addition, these classification processes may be performed as the defects are detected (i.e., real time defect classification (RTDC)).

Figures 6, 7:
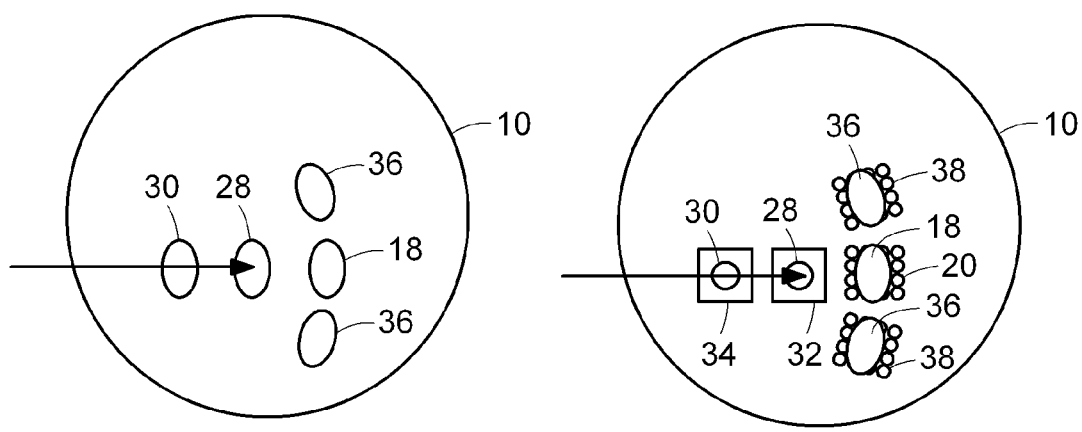
FIG. 6 is a partial schematic diagram of a top view of an embodiment of an inspection system, which includes side collectors configured to collect light scattered at different azimuthal angles.
FIG. 7 is a partial schematic diagram of a top view of the embodiment illustrated in FIG. 6, which includes side segmented detectors coupled to each of the side collectors.

Yet another embodiment is illustrated in FIG. 6. As shown in the partial schematic diagram of a top view of an inspection system illustrated in FIG. 6, the inspection system may include one or more side collectors 36. The side collectors may be configured to collect light scattered at different azimuthal angles than collector 18. The side collectors may or may not be configured to collect light scattered at the same polar angles as collector 18. The side collectors may be further configured as described above. Side detectors 38 may be coupled to each of the side collectors, as shown in FIG. 7. Side detectors 38 may be segmented collectors and may be configured as described above. For example, the side detectors may be configured to separately detect different portions of the light collected by the side collectors. In this manner, azimuthal and polar angular information about the different portions of the light collected by the side collectors is preserved. Side detectors 38 may also be configured to produce signals representative of the different portions of the light collected by the side collectors. Alternatively, the system may include optical or electronic components (not shown) coupled to side detectors 38 that can produce signals representative of the different portions of light detected by the side detectors. Signals from side detectors 38 may also be received by processor 26. Processor 26 may be configured to detect defects on the specimen from the signals as described herein.

Figure 8:
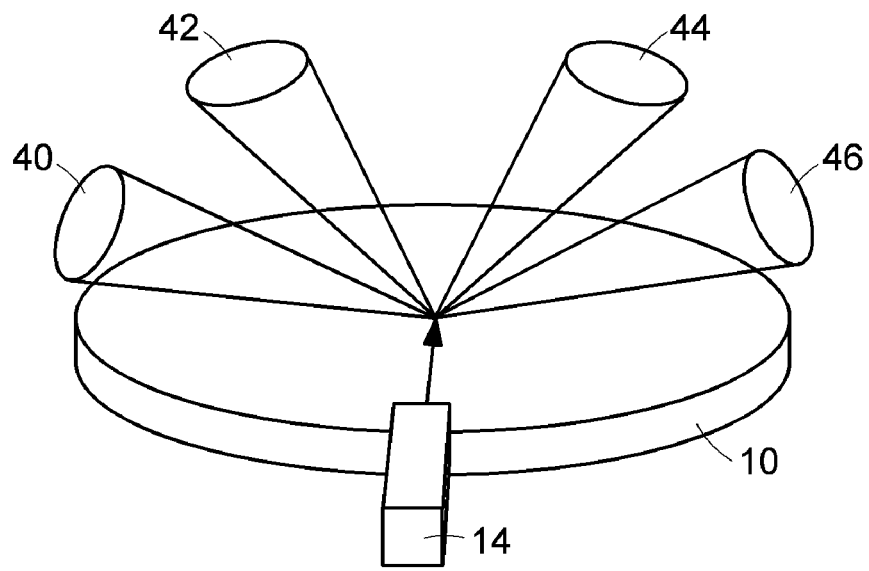
FIG. 8 is a partial schematic diagram of a perspective view of an embodiment of an inspection system, which includes azimuthally symmetrical collectors.

FIG. 8 illustrates another embodiment of an inspection system. This embodiment may be configured as described herein with exception to the differences between the collection system illustrated in FIG. 8 and the collectors illustrated in other figures. In this manner, several elements have been eliminated from FIG. 8 for clarity such as a light source and other components of the illumination system. Deflector 14 may scan a light beam over the specimen. The deflector may be configured as described above. For example, the deflector may scan the light beam over a wide scan angle on the specimen. Collectors 40, 42, 44, and 46 collect light scattered from the specimen as the specimen is scanned. Each of the collectors collect light over a fixed solid angle, depending upon the polar and azimuthal angle of the collector.

The collectors may be disposed symmetrically about the specimen. For example, collectors 40 and 46 may be located at approximately the same azimuthal angle on opposite sides of the plane of incidence. In one particular example, collectors 40 and 46 may be located at an azimuthal angle of about 75° to about 105° degrees with respect to the plane of incidence. In this manner, collectors 40 and 46 may be configured to collect light scattered forwardly and backwardly from the specimen. In addition, collectors 42 and 44 may be located at approximately the same azimuthal angle on opposite sides of the plane of incidence. For example, collectors 42 and 44 may be located at an azimuthal angle of about 30° to about 60° with respect to the plane of incidence. As such, collectors 42 and 44 may be configured to collect light scattered forwardly from the specimen. The four collectors may be arranged at elevation angles such that the collectors will collect light scattered at angles from about 3° to about 30° from the plane of the surface of the specimen. Although four collectors are shown in FIG. 8, it is to be understood that the system may include a greater number of collectors.

Each of the collectors may be coupled to a detector (not shown). At least one of the detectors may be segmented. For example, the detector coupled to collector 42 and/or collector 44 may be segmented. The detectors coupled to collectors 40 and 46 may or may not be segmented. The detectors may be further configured as described herein. In some embodiments, the collectors that are coupled to segmented collectors may provide a Fourier plane (not shown) such that Fourier filtering of the collected light may be performed as described above. In this manner, the Fourier components of the scattered light may be identified and eliminated as described herein prior to defect detection. In addition, the system illustrated in FIG. 8 may be further configured as described herein. For example, the system may include a stage, which may be configured to rotate and translate the specimen during inspection. Furthermore, the collection system illustrated in FIG. 8 may be further configured as illustrated in U.S. Pat. No. 5,864,394 to Jordan, III et al. and U.S. Pat. No. 6,081,325 to Leslie et al., which are incorporated by reference as if fully set forth herein. In addition, the inspection systems described herein may be further configured as, and include other elements of, the systems described in these patents.

Figure 9:
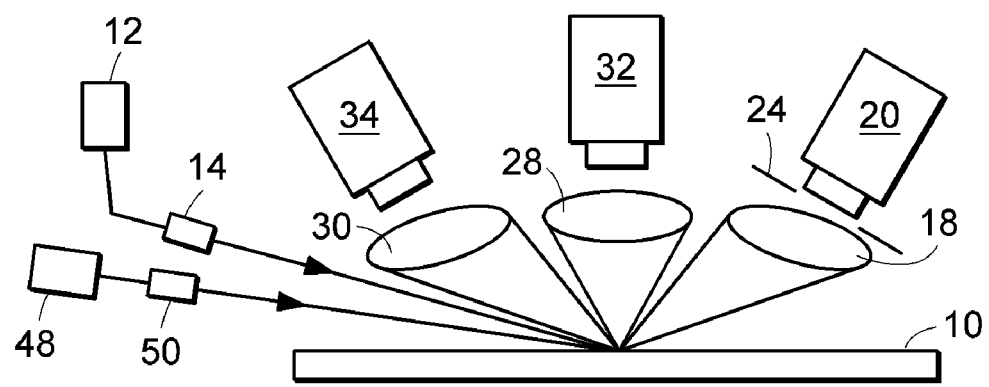
FIG. 9 is a partial schematic diagram of a side view of an embodiment of an inspection system, which is configured to direct two beams of light to a specimen.

FIG. 9 illustrates a schematic diagram of a side view of yet another embodiment of an inspection system. Certain elements of the inspection system have been eliminated from FIG. 9 for simplicity such as a processor. As shown in FIG. 9, the system includes an illumination system. The illumination system includes two light sources, 12 and 48. Light sources 12 and 48 may include any of the light sources described above. In addition, light sources 12 and 48 may be configured to emit light having substantially the same characteristics or light having different characteristics. For example, in one embodiment, light source 12 may be configured to emit light having approximately the same wavelength as light emitted by light source 48. In an alternative embodiment, light source 12 and light source 48 may emit light having different wavelengths. In yet other embodiments, light sources 12 and 48 may emit light having the same or different polarizations. The light sources may be configured to emit light having different characteristics such as wavelength and/or polarization such that scattered light originating from the two different light beams may be distinguished. In another embodiment, light sources 12 and 48 may be replaced by a single light source such as a laser source that can produce light having two distinct wavelengths (i.e., 488 nm and 514 nm). The illumination system may include a dichroic beamsplitter (not shown) that can produce two beams of light from the light emitted by the single light source. The two beams of light may then be directed to the surface of the specimen at different angles of incidence. Two beams of light having different polarizations may be produced and directed to the specimen at different angles of incidence in a similar manner. The illumination system may also include a number of other components which are not shown in FIG. 9 such as folding mirrors, beam splitters, spectral filters, and polarizing filters.

As further shown in FIG. 9, light source 12 may be coupled to deflector 14 and light source 48 may be coupled to deflector 50. In this manner, light from each light source may be scanned across the specimen. The light from each light source may be scanned over a wide scan angle on the specimen as described above. In alternative embodiments, light from light sources 12 and 48 may be stationary on the specimen while the specimen is translated (i.e., either rotationally and laterally or laterally in two directions). In such embodiments, the two beams of light may be configured to illuminate a relatively large elongated spot on the specimen or two different relatively large spots on the specimen. In this case, the plane of incidence of the illumination spot may be along a radius of the specimen, and collectors 20, 32, and 34 may also be in the plane of incidence. If the relatively large spot(s) are scanned over the specimen by the deflectors, the illumination direction, the place of incidence, and the collectors may be rotated about 90° such that the deflectors scan a relatively short line along a radius of the specimen and such that the beam of light out of the deflectors is approximately perpendicular to the short scan line. In some embodiments, the relatively large elongated spot may be about 50 μm to about 400 μm long. As shown in FIG. 9, light sources 12 and 48, deflectors 14 and 50, and various other components of the illumination system may be arranged such that the specimen may be illuminated by directing beams of light to the specimen at different angles of incidence.

Figure 10:
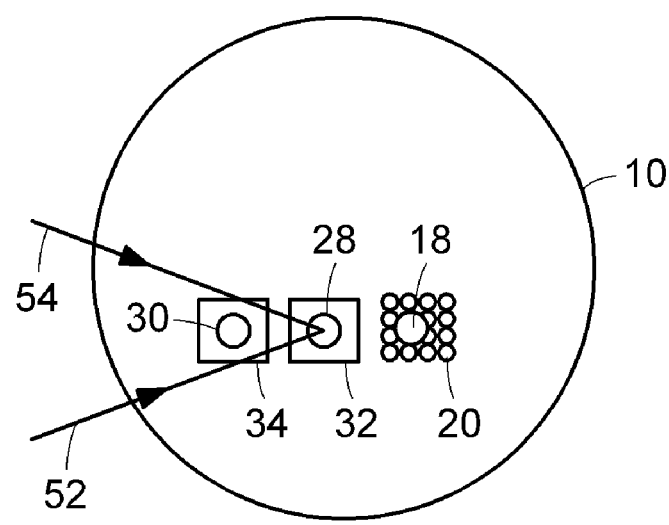
FIG. 10 is a partial schematic diagram of a top view of an embodiment of an inspection system, which is configured to direct two beams of light to a specimen.

FIG. 10 illustrates a partial schematic diagram of a top view of an additional embodiment of an inspection system. In this embodiment, light sources, deflectors, and various other components of the illumination system may be arranged such that the specimen may be illuminated by different beams of light 52 and 54 at different azimuthal angles. The illumination system of the system illustrated in FIG. 10 may or may not also be configured such that beams of light 52 and 54 are directed to the specimen at different angles of incidence. In some embodiments, therefore, the illumination system may be configured to illuminate the specimen by directing beams of light to the specimen at different angles of incidence and/or at different azimuthal angles. The different beams of light may have different wavelengths and/or polarizations as described above.

As further shown in FIGS. 9 and 10, the illumination system may be configured to illuminate the specimen by directing different beams of light (i.e., beams of light 52 and 54) to one spot on the specimen. In some embodiments, however, the illumination system may be configured to illuminate the specimen by directing different beams of light to different spots on the specimen. The embodiments shown in FIGS. 9 and 10 may be further configured as a dual oblique laser illumination system. One example of such an illumination system is illustrated in U.S. Pat. No. 6,288,780 B1 to Fairley et al., which is incorporated by reference as if fully set forth herein.

In some embodiments, the system may be configured such that two light beams having different wavelengths are incident on the surface of the specimen. In addition, the light beam which is incident on the specimen may be switched between the two illumination channels at a frequency higher than the data collection rate so that the data collected due to scattering from one light beam may be distinguished from data collected due to scattering from the other light beam. In one embodiment, the light sources may produce a modulated light beam. For example, a modulated light source may include, but is not limited to, a mode-locked laser, a pulsed laser, and a diode laser that is driven such that it is modulated. In another embodiment, the light beams may be modulated using, for example, a chopper (not shown). In the case of two light sources, each of which emit light having a different wavelength, a chopper may be disposed in the path of the light emitted by each light source. In the case of a single light source that produces light having two distinct wavelengths, a chopper may be disposed in the path of each light beam produced by a dichroic beamsplitter (not shown). In addition, any suitable modulator known in the art may be used in place of a chopper. In such an embodiment, a lock-in amplifier may be coupled to the detector(s). The lock-in amplifier may process the signals from the detector and may pass the processed signals on to the processor.

The two modulated beams of light may be directed to the surface of the specimen at different angles of incidence and/or different azimuthal angles as shown in FIGS. 9 and 10. Alternatively, the two modulated beams of light may be directed to the surface of the specimen at the same angle of incidence and/or the same azimuthal angle. For example, in one embodiment, the illumination system may include a number of light directing optical components downstream of the dichroic beamsplitter that are configured to direct the two beams of light to the specimen at the same angle of incidence.

In another embodiment, the angle of incidence and/or the azimuthal angle at which a beam of light is directed to the surface of the specimen may be modulated. For example, the light beam which is incident on the specimen may be switched between two angles of incidence at a frequency higher than the data collection rate so that the data collected due to scattering from one angle of incidence may be distinguished from data collected due to scattering from the other angle of incidence. In such an embodiment, two light beams may be directed to the specimen at different angles of incidence, and a chopper or another suitable modulator may be placed in the path of each of the light beams. In another embodiment, a Bragg modulator or an electro-optic modulator such as a Pockels cell may be placed between a single light source and other light directing optical components such as a polarizing beam splitter. In either of these embodiments, the light beams may be incident on the specimen at different times. Furthermore, in both embodiments, a lock-in amplifier may be coupled to the detector(s). The lock-in amplifier may process the signals from the detector and may pass the processed signals on to the processor. Examples of inspection systems configured to switch between normal and oblique illumination are illustrated in U.S. Pat. No. 6,201,601 B1 to Vaez-Iravani et al., which is incorporated by reference as if fully set forth herein. The system may be further configured as described in this patent.

In embodiments having frequency dependent illumination, the processor may be configured to analyze signals or data generated by inspection in time domain. In addition, in such embodiments, the processor may be configured to lock-in detection stack data. In this manner, data representing one area on the specimen that is generated using different illumination channels may be stacked or combined in another way such that the data may be analyzed simultaneously. Prior to locking the data into detection stacks, the processor may analyze the data by thresholding, which may be performed according to any of the embodiments described above. In addition, the locked-in detection stack data may be stored in memory for further processing. The memory may be a memory medium coupled to the processor or another suitable memory medium. Alternatively, the detection stack data may not be stored in memory before the data is further processed. The detection stack data may be further processed according to any of the embodiments described above (i.e., 1D filtering, 2D filtering, comparison, etc.).

Figure 11:
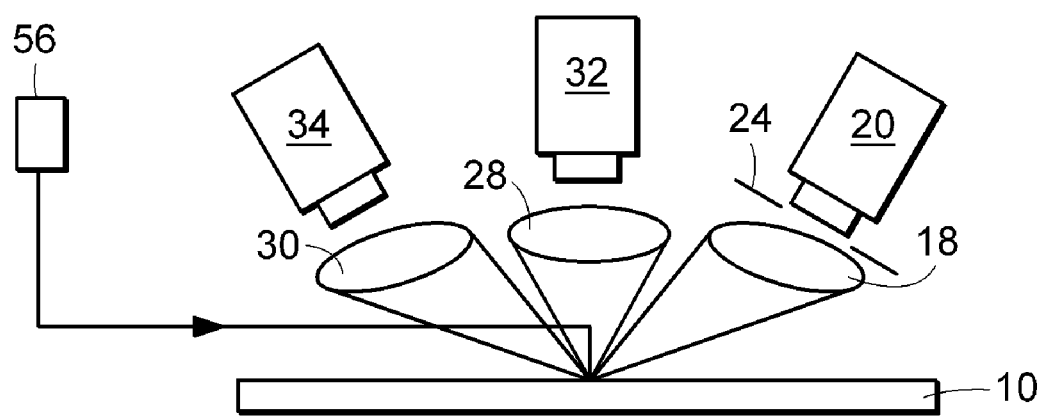
FIG. 11 is a partial schematic diagram of a side view of an embodiment of an inspection system, which is configured to illuminate a specimen at a normal angle of incidence.

FIG. 11 illustrates a partial schematic diagram of a side view of an alternative embodiment of an inspection system.

In this embodiment, the illumination system of the inspection system includes light source 56. Light source 56 may include any of the light sources described herein. This illumination system may also include a number of other components which are not shown in FIG. 11 such as folding mirrors, beam splitters, spectral filters, and polarizing filters. Light source 56 and various other components of the illumination system may be configured such that the illumination system illuminates the specimen at a substantially normal angle of incidence. In this manner, the illuminated portion of the specimen may be a circular spot. Such illumination may be particularly suitable for defect detection using die:die inspection or array inspection. In one such embodiment, a stop may be coupled to the center collector to block specular reflection of the normal incident beam from the detector coupled to the center collector.

The system shown in FIG. 11 may be advantageous for distinguishing between micro-scratches and particles. For example, the scattering pattern due to a micro-scratch produces the highest concentration of energy and greatest detection uniformity when illuminated normal and captured in the near normal or narrow channel collected by the center collector. The unique signature of the micro-scratch in the form of an elongated pattern in the far-field allows for a simple method of classification.

In addition, the illumination system may be configured to illuminate the specimen at a substantially normal angle of incidence with a stationary light beam. For example, as shown in FIG. 11, the illumination system does not include any deflectors that may scan the light beam over the specimen. Instead, the specimen may be scanned by relative motion of the specimen caused by a stage, which may be configured as described above. In some embodiments, the illumination system may be configured such that the stationary light beam illuminates a relatively large spot on the specimen. In other alternatives, the specimen may be scanned by relative motion of the illumination system caused by a controller (not shown) in addition to, or instead of, relative motion of the specimen caused by the stage. In some embodiments, the illumination system shown in FIG. 11 may also be configured to illuminate the specimen with an additional beam of light (not shown). The additional beam of light may be directed to the specimen at an oblique angle of incidence.

In another embodiment, the inspection system illustrated in FIG. 11 may be modified such that the inspection system may be used to detect macro defects. In one such embodiment, the system may be used as an after develop inspection (ADI) system. For example, center collector 28 may be replaced with a collimation lens. In one embodiment, the incident light may be directed to the specimen through the collimation lens. In this manner, the spot size of the incident light on the specimen may be substantially increased. Light reflected from the specimen may be collected by the collimation lens and may be imaged onto detector 32. In this embodiment, detector 32 is preferably a segmented detector such as an array detector. In another embodiment, an array of lenses (not shown) may be configured to focus light from the collimation lens to an array of individual spots on the surface of the specimen. Light reflected from each of the individual spots may be collected by the array of lenses, which may be directed to the detector by the collimation lens.

In the above embodiments, the reflectance at a plurality of locations on the specimen may be measured simultaneously. In addition, the reflectance at a plurality of locations may be measured as a function of wavelength. For example, the normal incidence light source may be a broadband light source coupled to a monochromator or a plurality of spectral filters. In this manner, the reflectance may be measured at multiple wavelengths separately. The measured reflectance data may be compared with a library of spectral data, and the thickness at each measurement point may be determined using a least squares fit method. Alternatively, the measured reflectance data may be compared with reference data obtained by measuring a reference specimen having a range of known thicknesses. Furthermore, any other method known in the art for determining a thickness of a thin film based on reflectance data may be used to determine a thickness of a layer on specimen 10. Therefore, the system illustrated in FIG. 11 may be configured to quickly measure thickness of a layer at multiple points on a specimen. As such, the system illustrated in FIG. 11 may be used to quickly detect macro defects on a specimen after a process step such as a develop step of a lithography process. Furthermore, the system shown in FIG. 11 may be used to generate a 2D map of thickness as a function of position across a specimen. In addition, since the system may be configured to illuminate a number of spots on a specimen with relatively high resolution, the system may be configured to generate a relatively high resolution map of the specimen. The system illustrated in FIG. 11 may be further configured as described in U.S. Pat. No. 5,543,919 to Mumola, U.S. Pat. No. 5,555,472 to Clapis et al., U.S. Pat. No. 5,555,474 to Ledger, and U.S. Pat. No. 5,563,709 to Poultney, which are incorporated by reference as if fully set forth herein.

In additional embodiments, the system illustrated in FIG. 11 may be used to determine additional properties from the measured spectral reflectance. For example, the system illustrated in FIG. 11 may be used to determine critical dimension and/or overlay of patterned features formed on the specimen. In one embodiment, a model method by modal expansion ("MMME") model may be used to generate a library of various reflectance spectrums. The MMME model is a rigorous diffraction model that may be used to calculate the theoretical diffracted light "fingerprint" from patterned features in the parameter space. Alternative models may also be used to calculate the theoretical diffracted light, however, including, but not limited to, a rigorous coupling waveguide analysis ("RCWA") model. The measured reflectance spectrum may be fitted to the various reflectance spectrums in the library. The fitted data may be used to determine a critical dimension such as a lateral dimension, a height, and a sidewall angle of a feature on a specimen. Examples of modeling techniques are illustrated in PCT Application No. WO 99/45340 to Xu et al., which is incorporated by reference as if fully set forth herein. Furthermore, the system shown in FIG. 11 may include polarizing elements such that $R_s$, $R_p$, and functions thereof may be measured separately.

Figure 12:
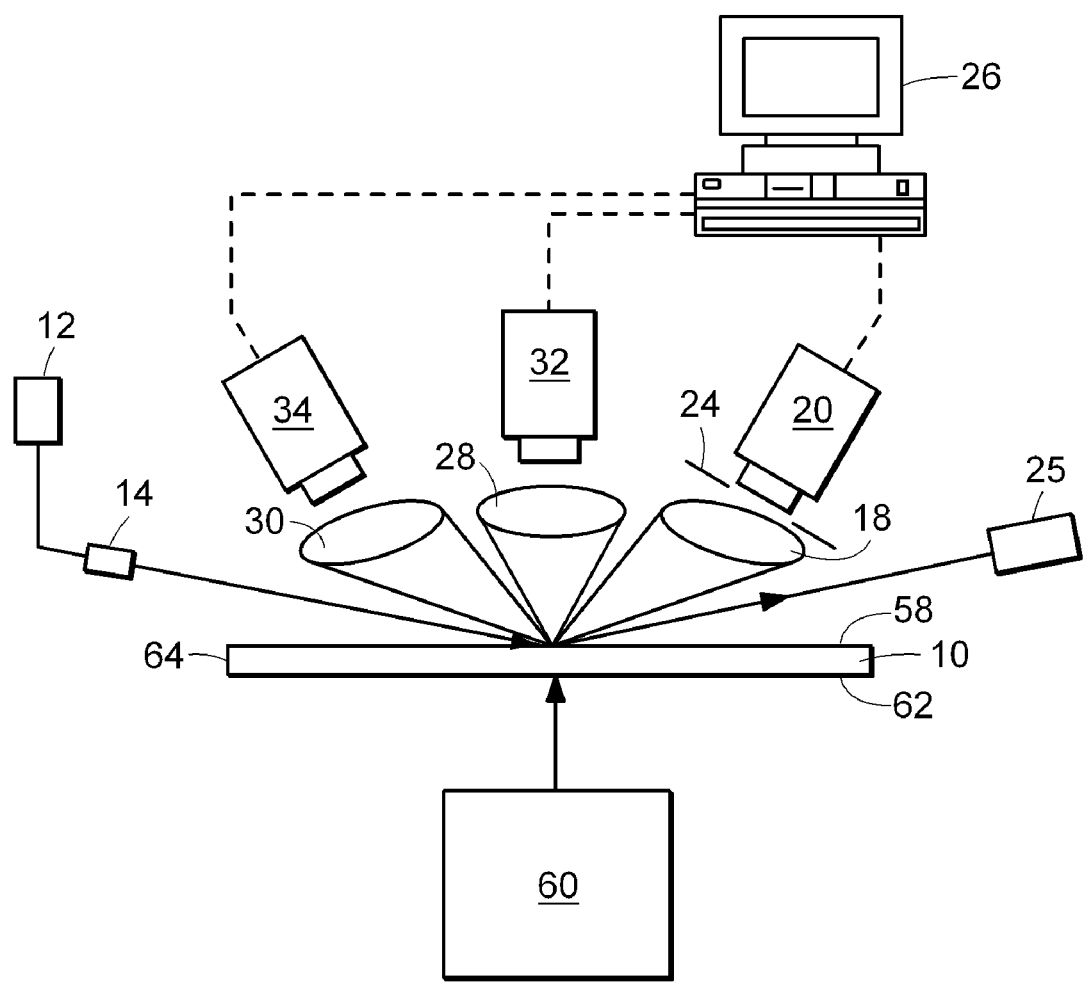
FIG. 12 is a partial schematic diagram of a side view of an embodiment of an inspection system, which is configured to detect defects on two surfaces of the specimen.

FIG. 12 illustrates a partial schematic diagram of an additional embodiment of an inspection system. The illumination system of the inspection system illustrated in FIG. 12 may be configured to illuminate first surface 58 of specimen 10. For example, light source 12, deflector 14, and any other components of the illumination system may be configured to scan a light beam over the first surface of the specimen. The illumination system, however, may be configured according to any of the embodiments described herein. In addition, the inspection system includes various other components such that defects may be detected on the first surface of the specimen. Although the portion of the inspection system configured for inspection of the first surface of the specimen are illustrated in FIG. 12 as shown in FIG. 1, it is to be understood that this portion of the system may be configured according to any other embodiment described herein.

As further shown in FIG. 12, the inspection system includes optical subsystem 60. Optical subsystem 60 is configured to detect defects on second surface 62 of the specimen. As shown in FIG. 12, first surface 58 and second surface 62 are opposite sides of specimen 10. In one embodiment, first surface 58 may be a patterned surface of the specimen since the elements of the inspection system arranged on this side of the specimen may be particularly suitable for the inspection of patterned surfaces as described above. In addition, second surface 62 may be a patterned surface or an unpatterned surface such as the backside of a semiconductor wafer. In other embodiments, the optical subsystem may be arranged such that a different surface of the specimen may be inspected. For example, in one embodiment, the optical subsystem may be arranged such that side surface 64 (i.e., a surface of the specimen arranged at an angle to the front surface) or an "edge" of the specimen may be inspected by the optical subsystem.

The inspection system of FIG. 12 may, therefore, by configured to inspect more than one surface of a specimen simultaneously. However, it is to be understood that the inspection system illustrated in FIG. 12 may also be configured to inspect more than one surface of the specimen sequentially if desired. The optical subsystem may be configured similar to or different than the components arranged to inspect the first surface of the specimen. For example, the optical subsystem may be configured according to any of the embodiments described herein. Alternatively, the optical subsystem may include any other optical subsystem known in the art such as an optical subsystem that is suitable for the inspection of the backside of wafers or unpatterned surfaces.

In another embodiment, any of the inspection systems described herein may be configured to inspect more than one surface of the specimen. For example, the inspection systems may includes a mechanical device that may be configured to change the surface of the specimen that is inspected by the system. For example, the inspection system may include a Back Side Inspection Module (BSIM), which is commercially available from KLA-Tencor, San Jose as part of the SP1 laser-based wafer inspection tool. The BSIM enables non-destructive frontside and backside inspection of a specimen such as a wafer through wafer edge handling and a "flipping" mechanism. Therefore, the wafer handling is designed such that the frontside of the wafer is not damaged during inspection of the backside of the wafer. In this manner, backside inspection of both product and non-product wafers may be performed by the inspection system.

As described above, the inspection systems described herein are configured to inspect patterned wafers. In one embodiment, the patterned wafers may be product wafers. "Product wafers" are generally defined as semiconductor wafers upon which semiconductor devices may ultimately be formed. Therefore, inspecting product wafers during or after semiconductor fabrication processes performed on the wafers may be important for monitoring the processes and tools involved in the processes. In this manner, the inspection system may be utilized as a tool monitor (TM) system, which may be used to ensure yield by inspection of product wafers.

In another embodiment, the inspection systems described herein are also suitable for inspection of monitor wafers. "Monitor wafers" are generally defined as semiconductor wafers that have been run through a process tool, but upon which semiconductor devices are not ultimately formed. Repetitive pattern features are not usually formed on monitor wafers. Monitor wafers are generally used as a gauge for the number and types of defects that may be found on product wafers. Therefore, inspecting monitor wafers during or after semiconductor fabrication processes performed on the wafers may be important for qualifying the processes and tools involved in the processes. In this manner, the inspection system may be utilized as a tool qualifying (TQ) system, which may be used to ensure yield by inspection of monitor wafers.

In one embodiment, an inspection system as described herein may be coupled to a process tool. For example, the inspection system may be disposed within the process tool. In some such embodiments, the inspection system may be integrated into the process tool such that a product wafer may be inspected prior to, during, or after a step of the process. In other embodiments, the inspection system may be coupled to the process tool by a common handler, a common power source, a common processor, or a common environment. For example, the inspection system may be a separate module or tool that is coupled to the process tool by a common handler.

In yet other embodiments, the inspection system may be a "stand alone tool" or a tool that is not physically coupled to a process tool. Such an inspection system, however, may be coupled to the process tool by a transmission medium, which may include wired and wireless portions.

The process tool may include any process tool known in the art such as a lithography tool, an etch tool, a deposition tool, a polishing tool, a plating tool, a cleaning tool, or an ion implantation tool. The process tool may be a "cluster tool" or a number of process modules coupled by a common handler. The results of the inspection may be used to alter a parameter of a process or a process tool using a feedback control technique, a feedforward control technique, or an in situ control technique. The parameter of the process or the process tool may be altered manually or automatically.

Further modifications and alternative embodiments of various aspects of the invention may be apparent to those skilled in the art in view of this description. For example, systems for inspecting patterned and unpatterned wafers or other specimen are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An inspection system, comprising:
   an illumination system configured to illuminate a specimen;
   a collector configured to collect light scattered from the specimen;
   a segmented detector configured to separately detect different portions of the light such that azimuthal and polar angular information about the different portions of the light is preserved and to produce signals representative of the different portions of the light; and a processor configured to detect defects on the specimen from the signals.

2. The system of claim 1, wherein an axis of the collector is centered in the plane of incidence at about 60° to about 80° from normal.

3. The system of claim 1, wherein the collector provides a Fourier plane suitable for Fourier filtering of the light.

4. The system of claim 1, further comprising a plurality of fibers configured to separately convey the different portions of the light to the detector.

5. The system of claim 1, wherein the detector comprises an array detector.

6. The system of claim 1, wherein the detector comprises a multi-anode photo-multiplier tube.

7. The system of claim 1, further comprising a side collector configured to collect light scattered at different azimuthal angles than the collector, and a side segmented detector configured to separately detect different portions of the light collected by the side collector such that azimuthal and polar angular information about the different portions of the light collected by the side collector is preserved and to produce signals representative of the different portions of the light collected by the side collector.

8. The system of claim 1, wherein the illumination system is further configured to illuminate the specimen by scanning a light beam over the specimen.

9. The system of claim 1, wherein the illumination system is further configured to illuminate the specimen by scanning a light beam over a wide scan angle on the specimen while the specimen is translated and rotated.

10. The system of claim 1, wherein the illumination system is further configured to illuminate the specimen at an oblique angle of incidence.

11. The system of claim 1, wherein the illumination system is further configured to illuminate the specimen by directing different beams of light to the specimen at different angles of incidence or at different azimuthal angles.

12. The system of claim 1, wherein the illumination system is further configured to illuminate the specimen by directing different beams of light to one spot on the specimen.

13. The system of claim 1, wherein the illumination system is further configured to illuminate the specimen at a normal angle of incidence.

14. The system of claim 1, wherein the illumination system is further configured to illuminate the specimen with a stationary light beam.

15. The system of claim 1, further comprising a stage configured to rotate and translate the specimen during inspection.

16. The system of claim 1, further comprising a stage configured to translate the specimen in two lateral directions during inspection.

17. The system of claim 1, wherein the specimen comprises a patterned wafer.

18. The system of claim 1, wherein the illumination system is further configured to illuminate a first surface of the specimen, the system further comprising an optical subsystem configured to detect defects on a second surface of the specimen.

19. An inspection system, comprising:
an illumination system configured to illuminate a specimen;
a front collector configured to collect light scattered forwardly from the specimen;
a center collector configured to collect light scattered forwardly and backwardly from the specimen;
a back collector configured to collect light scattered backwardly from the specimen;
a segmented detector configured to separately detect different portions of the light collected by the front collector such that azimuthal and polar angular information about the different portions of the light is preserved and to produce signals representative of the different portions of the light; and
a processor configured to detect defects on the specimen from the signals.

20. The system of claim 19, wherein an axis of the front collector is centered in the plane of incidence at about 60° to about 80° from normal.

21. The system of claim 19, wherein the front collector provides a Fourier plane suitable for Fourier filtering of the light collected by the front collector.

22. The system of claim 19, wherein axes of the front, center, and back collectors are centered in the plane of incidence.

23. The system of claim 19, further comprising a plurality of fibers configured to separately convey the different portions of the light to the detector.

24. The system of claim 19, wherein the detector comprises an array detector.

25. The system of claim 19, wherein the detector comprises a multi-anode photo-multiplier tube.

26. The system of claim 19, further comprising a side collector configured to collect light scattered forwardly from the specimen at different azimuthal angles than the light collected by the front collector, and a side segmented detector configured to separately detect different portions of the light collected by the side collector such that azimuthal and polar angular Information about the light collected by the side collector is preserved and to produce signals representative of the different portions of the light collected by the side collector.

27. The system of claim 19, wherein the illumination system is further configured to illuminate the specimen by scanning a light beam over the specimen.

28. The system of claim 19, wherein the illumination system is further configured to illuminate the specimen by scanning a light beam over a wide scan angle on the specimen while the specimen is translated and rotated.

29. The system of claim 19, wherein the illumination system is further configured to illuminate the specimen by directing different beams of light to the specimen at different oblique angles of incidence or at different azimuthal angles.

30. The system of claim 19, wherein the illumination system is further configured to illuminate the specimen by directing different beams of light to one spot on the specimen.

31. The system of claim 19, wherein the illumination system is further configured to illuminate the specimen at a normal angle of incidence.

32. The system of claim 19, wherein the illumination system is further configured to illuminate the specimen with a stationary light beam.

33. The system of claim 19, further comprising a stage configured to rotate and translate the specimen during inspection.

34. The system of claim 19, further comprising a stage configured to translate the specimen in two lateral directions during inspection.

35. The system of claim 19, wherein the specimen comprises a patterned wafer.

36. The system of claim 19, wherein the illumination system is further configured to illuminate a first surface of the specimen, the system further comprising an optical subsystem configured to detect defects on a second surface of the specimen.

37. An inspection system, comprising:
- a stage configured to rotate and translate a specimen, wherein the specimen comprises a patterned wafer; and
- an illumination system configured to scan the specimen in a wide scan path during rotation and translation of the specimen;
- a collector configured to collect light scattered from the specimen;
- a segmented detector configured to separately detect different portions of the light such that azimuthal and polar angular information about the different portions of the light is preserved and to produce signals representative of the different portions of the light; and
- a processor configured to detect defects on the specimen from the signals.

38. The system of claim 37, wherein the wide scan path is greater than about 0.1 radians.

39. The system of claim 37, wherein the illumination system comprises an acousto-optical deflector.

* * * * *